US011351225B2

(12) United States Patent
Haider

(10) Patent No.: US 11,351,225 B2
(45) Date of Patent: Jun. 7, 2022

(54) METHODS FOR MODULATING DEVELOPMENT AND FUNCTION OF PHOTORECEPTOR CELLS

(71) Applicant: The Schepens Eye Research Institute, Inc., Boston, MA (US)

(72) Inventor: Neena B. Haider, Brookline, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 15/818,470

(22) Filed: Nov. 20, 2017

(65) Prior Publication Data

US 2018/0271941 A1    Sep. 27, 2018

Related U.S. Application Data

(63) Continuation of application No. 14/772,039, filed as application No. PCT/US2014/020038 on Mar. 3, 2014, now Pat. No. 9,855,314.

(60) Provisional application No. 61/771,503, filed on Mar. 1, 2013.

(51) Int. Cl.
| | |
|---|---|
| *C07H 21/04* | (2006.01) |
| *A61K 38/17* | (2006.01) |
| *A61K 48/00* | (2006.01) |
| *C07K 14/47* | (2006.01) |
| *A61K 31/13* | (2006.01) |
| *C12N 5/10* | (2006.01) |

(52) U.S. Cl.
CPC .......... *A61K 38/1783* (2013.01); *A61K 31/13* (2013.01); *A61K 48/005* (2013.01); *A61K 48/0083* (2013.01); *C07K 14/4705* (2013.01); *C12N 5/10* (2013.01); *H05K 999/99* (2013.01); *A61K 48/00* (2013.01)

(58) Field of Classification Search
CPC .... A61K 31/713; C12N 15/111; C12N 15/113
See application file for complete search history.

(56) References Cited

U.S. PATENT DOCUMENTS

| 9,855,314 B2 | 1/2018 | Haider | |
|---|---|---|---|
| 2005/0158771 A1* | 7/2005 | Clerc | A61P 43/00 435/6.11 |
| 2005/0277868 A1 | 12/2005 | Heller et al. | |
| 2007/0015238 A1 | 1/2007 | Snyder et al. | |
| 2007/0083334 A1 | 4/2007 | Mintz et al. | |

FOREIGN PATENT DOCUMENTS

| WO | 00/15822 A1 | 3/2000 |
|---|---|---|
| WO | 2005/076004 A1 | 8/2005 |
| WO | 2014/134627 A1 | 9/2014 |

OTHER PUBLICATIONS

Strausberg et al. (Proc. Natl. Acad. Sci. U.S.A. 99 (26), 16899-16903 (2002)).*
Mollema et al. (PLoS ONE, 2011, vol. 6, issue 3, e17494, pp. 1-10).*
Wolf (Sep. 1997) "Identical mutation and phenotypic variation", Human Genetics, 100(3-4):305-321.
Yanagi et al. (Nov. 2000) "Distinct functions of photoreceptor cell-specific nuclear receptor, thyroid hormone receptor beta2 and CRX in one photoreceptor development", Investigative Ophthalmology & Visual Science, 43(11):3489-3494.
Zamir et al. (Oct. 1996) "A nuclear hormone receptor corepressor mediates transcriptional silencing by receptors with distinct repression domains", Nature Reviews Molecular Cell Biology, 16(10):5458-5465.
Zernant et al. (Sep. 2005) "Genotyping microarray (disease chip) for Leber congenital amaurosis: detection of modifier; alleles", Investigative Ophthalmology & Visual Science, 46(9):3052-3059.
Zoller et al. (Oct. 25, 1982) "Oligonucleotide-directed mutagenesis using M13-derived vectors: an efficient and general procedure for the production of point mutations in any fragment of DNA", Nucleic Acids Research, 10(20):6487-6500.
Li et al. (Mar. 2, 2020) "Nr2e3 is a genetic modifier that rescues retinal degeneration and promotes homeostasis in multiple models of retinitis pigmentosa", Gene Therapy, doi.org/10.1038/s41434-020-0134-z.
Adelman et al. (1983) "In vitro deletional mutagenesis for bacterial production of the 20,000-dalton form of human pituitary growth hormone", DNA, 2(3):183-193.
Adelmant et al. (Apr. 16, 1996) "A functional Rev-erb alpha responsive element located in the human Rev-erb alpha promoter mediates a repressing activity", PNAS, 93(8):3553-3558.
Akhmedov et al. (May 9, 2000) "A deletion in a photoreceptor-specific nuclear receptor mRNA causes retinal degeneration in the rd7 mouse", PNAS, 97(10):5551-5556.
Altschul et al. (Oct. 1990) "Basic local alignment search tool", Journal of Molecular Biology, 215(3):403-410.
Altschul et al. (Sep. 1, 1997) "Gapped BLAST and PSI-BLAST: a New Generation of Protein Database Search Programs", Nucleic Acids Research, 25(17):3389-3402.
Aukunuru et al. (Sep. 2003) "Nanoparticle formulation enhances the delivery and activity of a vascular endothelial growth factor antisense oligonucleotide in human retinal pigment epithelial cells", Journal of Pharmaceutical Sciences, 55(9):199-1206.
Bandah et al. (Mar. 2009) "The spectrum of retinal diseases caused by NR2E3 mutations in Israeli and Palestinian patients". Archives of Ophthalmology, 127(3):297-302.
Burris (Jul. 1, 2008) "Nuclear hormone receptors for heme: REV-ERBalpha and REV-ERBbeta are ligandregulated components of the mammalian clock", Molecular Endocrinology, 22(7):1509-1520.
Cheng et al. (Aug. 1, 2005) "Photoreceptor-specific nuclear receptor NR2E3 functions as a transcriptional activator in rod photoreceptors", Human Molecular Genetics, 13(15):1563-1575.

(Continued)

*Primary Examiner* — Amy H Bowman
(74) *Attorney, Agent, or Firm* — Don D. Cha; HDC Intellectual Property Law, LLP

(57) ABSTRACT

The present invention relates to compositions and methods comprising administering gene modifiers for treating ocular disease.

18 Claims, 15 Drawing Sheets

Specification includes a Sequence Listing.

(56) References Cited

OTHER PUBLICATIONS

Cheng et al. (Sep. 1, 2006) "In vivo function of the orphan nuclear receptor NR2E3 in establishing photoreceptor; identity during mammalian retinal development", Human Molecular Genetics, 15(17):2588-2602.
Cideciyan et al. (Aug. 2009) "Vision 1 year after gene therapy for Leber's congenital amaurosis", The New England Journal of Medicine, 361(7):725-727.
Cideciyan et al. (Sep. 2009) "Human RPE65 gene therapy for Leber congenital amaurosis: persistence of early visual improvements and safety at 1 year", Human Gene Therapy, 20(9):999-1004.
Collaco et al. (Nov. 2008) "Update on gene modifiers In cystic fibrosis", Current Opinion in Pulmonary Medicine, 14(6):559-566.
Coppieters et al. (Jul. 2007) "Recurrent mutation in the first zinc finger of the orphan nuclear receptor NR2E3 causes autosomal dominant retinitis pigmentosa", American Journal of Human Genetics, 81(1):147-157.
Corbo et al. (Aug. 2005) "A hybrid photoreceptor expressing both rod and cone genes in a mouse model of enhanced S-cone syndrome", PLOS Genetics, 1(2), e11:18 pages.
Cruz et al. (Jan. 31, 2014) "Modifier genes as therapeutics: the nuclear hormone receptor Rev Erb alpha (Nr1 d1) rescues Nr2e3 associated retinal disease", PLoS One, 9(1):9 pages.
Cutting (2005) "Modifier genetics: cystic fibrosis", Annual Review of Genomics and Human Genetics, 6:237-260.
Cutting (Dec. 2010) "Modifier genes in Mendelian disorders: the example of cystic fibrosis", Annals of the New York Academy of Sciences, 1214:57-69.
Escher et al. (Mar. 2009) "Mutations in NR2E3 can cause dominant or recessive retinal degenerations in the same family", Human Mutation, 30(3):342-351.
Fahim et al. (Aug. 12, 2011) "Allelic heterogeneity and genetic modifier loci contribute to clinical variation in males with X-linked retinitis pigmentosa due to RPGR mutations", PLOS One, 6(8), e23021:11 pages.
GENBANK (Mar. 12, 2011) "*Homo sapiens* nuclear receptor Rev-ErbA-alpha (NR1D1) mRNA, complete cds", GENBANK Accession No. HQ692861.1, 2 pages.
Gerber et al. (Sep. 2000) "The photoreceptor cell-specific nuclear receptor gene (PNR) accounts for retinitis pigmentosa in the Crypto-Jews from Portugal (Marranos), survivors from the Spanish Inquisition", Human genetics, 107(3):276-284.
Gire et al. (Oct. 17, 2007) "The Gly56Arg mutation in NR2E3 accounts for 1-2% of autosomal dominant retinitis pigmentosa", Molecular Vision, 13:1970-1975.
Haider et al. (Feb. 2000) "Mutation of a nuclear receptor gene, NR2E3, causes enhanced Scone syndrome", Nature Genetics, 24(2):127-131.
Haider et al. (Feb. 22, 2002) "Genetic modifiers of vision and hearing", Human Molecular Genetics, 11(10):1 195-1206.
Haider et al. (Jun. 8, 2001) "Excess cone cell proliferation due to lack of a functional NR2E3 causes retinal dysplasia and degeneration in rd7/rd7 mice", Human Molecular Genetics, 10(16):1619-1626.
Haider et al. (Mar. 2008) "Mapping of genetic modifiers of Nr2e3 rd7/rd7 that suppress retinal degeneration and restore blue cone cells to normal quantity", Mammalian Genome, 19(3):145-154.
Haider et al. (Nov. 2006) "The transcription factor Nr2e3 functions in retinal progenitors to suppress cone cell generation", Visual Neuroscience, 23(6):917-929.
Haider et al. (Sep. 2009) "Nr2e3-directed transcriptional regulation of genes involved in photoreceptor development and cell-type specific phototransduction", Experimental Eye Research, 89(3):365-372.
Hamilton et al. (Apr. 12, 2012) "Modifier genes and the plasticity of genetic networks in mice", PLOS Genetics. 8(4), e1002644, 11 pages.
Houlston et al. (Jan. 1998) "Modifier genes in humans: strategies for identification", European Journal of Human Genetics, 6(1):80-88.
Jacobson et al. (Jan. 2012) "Gene therapy for leber congenital amaurosis caused by RPE65 mutations: safety and efficacy in fifteen children and adults followed up to three years", Archives of Ophthalmology, 130(1):9-24.
Kakizawa et al. (May 2007) "Two differentially active alternative promoters control the expression of the zebrafish orphan nuclear receptor gene Rev-erbalpha", Journal of Molecular Endocrinology, 38(5):555-568.
Kay et al. (Jan. 2001) "Viral vectors for gene therapy: the art of turning infectious agents into vehicles of therapeutics", Nature Medicine, 7(1):33-40.
Kremers (Sep. 2003) "The assessment of L- and M-cone specific electroretinographical signals in the normal and abnormal human retina", Progress in Retinal and Eye Research, 22(5):579-605.
Kulkarni et al. (2014) "Nanoparticles for drug and gene delivery in treating diseases of the eye", Methods In Pharmacology And Toxicology, 291-316.
Maguire et al. (May 22, 2008) "Safety and efficacy of gene transfer for Leber's congenital amaurosis", The New England Journal of Medicine, 358(21):2240-2248.
Matsuda et al. (Jan. 16, 2007) "Controlled expression of transgenes introduced by in vivo electroporation", PNAS, 104(3):1027-1032.
Myers et al. (Mar. 1988) "Optimal alignments in linear space", Computer Applications in the Biosciences, 4(1):11-17.
Needleman et al. (Mar. 28, 1970) "A general method applicable to the search for similarities in the amino acid sequence of two proteins", Journal of Molecular Biology, 48(3):443-453.
Passerini et al. (Nov.-Dec. 2007) "Phenotypic Intrafamilial variability Associated with S212G Mutation in the RDS/peripherin Gene", European Journal of Ophthalmology, 17(6):1000-1003.
Peng et al. (Mar. 15, 2005) "The photoreceptor-specific nuclear receptor Nr2e3 interacts with Crx and exerts opposing effects on the transcription of rod versus cone genes", Human Molecular Genetics, 14(6):747-764.
Perlman (May 1, 2001) "The Electroretinogram: ERG By Ido Perlman", The Organization of the Retina and Visual System, 25 pages.
Schorderet et al. (Nov. 2009) "NR2E3 mutations in enhanced S-cone sensitivity syndrome (ESCS), Goldmann-Favre syndrome (GFS), clumped pigmentary retinal degeneration (CPRD), and retinitis pigmentosa (RP)", Human Mutation, 30(11):1475-1485.
Sharon et al. (Sep. 2003) "Shared mutations in NR2E3 in enhanced S-cone syndrome, Goldmann-Favre syndrome, and many cases of clumped pigmentary retinal degeneration", Archives of Ophthalmology, 121(9):1316-1323.
Simonelli et al. (Mar. 2010) "Gene therapy for Leber's congenital amaurosis is safe and effective through 1.5 years after vector administration", Molecular Therapy, 18(3):643-650.
Singh et al. (May 2009) "Intravenous transferrin, RGD peptide and dual-targeted nanoparticles enhance anti-VEGF intraceptor gene delivery to laser-induced CNV", Gene Therapy, 16(5):645-659.
Walia et al. (Mar. 2008) "Discordant phenotypes in fraternal twins having an identical mutation in exon ORF15 of the RPGR gene", Archives of Ophthalmology, 126(3):379-384.
Walther et al. (Aug. 2000) "Viral vectors for gene transfer: a review of their use in the treatment of human diseases", Drugs, 60(2):249-271.
Webber et al. (Jul. 2008) "Dual role of Nr2e3 in photoreceptor development and maintenance", Experimental Eye Research, 87(1):35-48.

\* cited by examiner

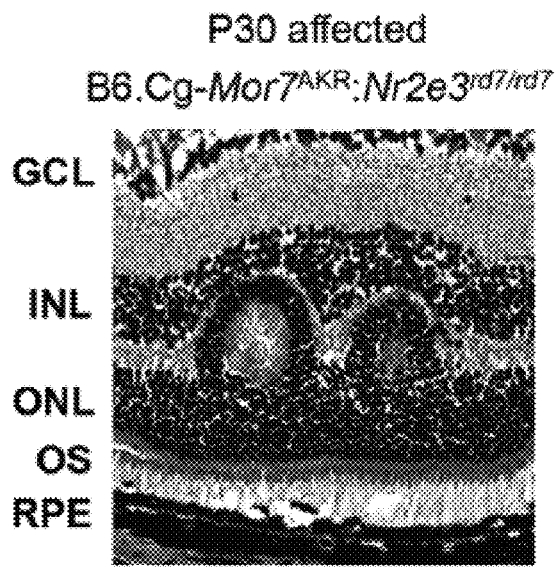 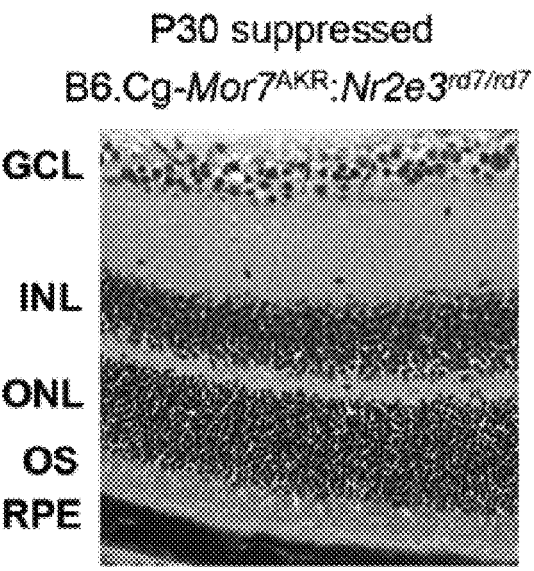
FIG. 1A  FIG. 1B
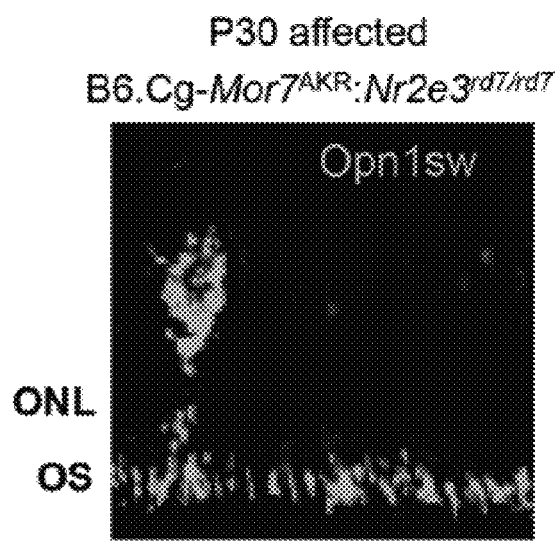 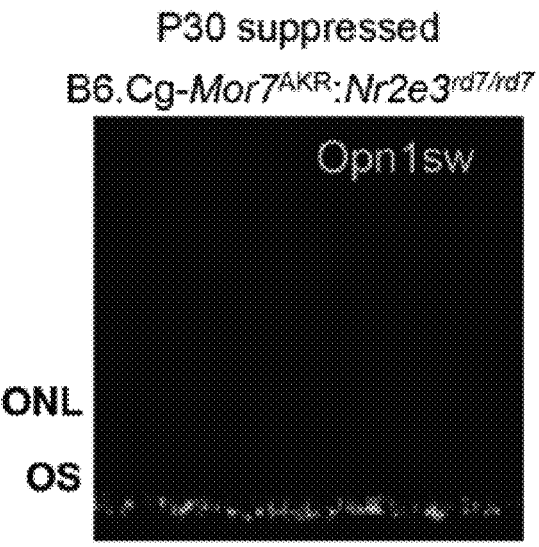
FIG. 1C  FIG. 1D

C57BL/6J

AKR/J

```
                         408
                          |
C57BL/J      PEGEAPANSLRQGNTKNVLLA    SEQ ID NO: 18
AKR/J        PEGEAPANSLQQGNTKNVLLA    SEQ ID NO: 19
Rat          PEGKAPANGLRQGNTKNVLLA    SEQ ID NO: 20
Chimpanzee   PEGKAPANSPRQGNSKNVLLA    SEQ ID NO: 21
Human        PEGKAPANSPRQGNSKNVLLA    SEQ ID NO: 22
             ***:****.  :***:******
```

```
             +494
              |
C57BL/J   AACTGCGGGGCTCACTCGTCT   SEQ ID NO: 23
AKR/J     AACTGCGGGGTTCACTCGTCT   SEQ ID NO: 24
Rat       AACTGCGGGCTTCACTCGTCT   SEQ ID NO: 25
Chimpanzee AGTCGCGGGGTCCACTCCCCG  SEQ ID NO: 26
Human     AGTCGCGGGGTCCACTCCCCG   SEQ ID NO: 27
           *  *****  *****    *
```

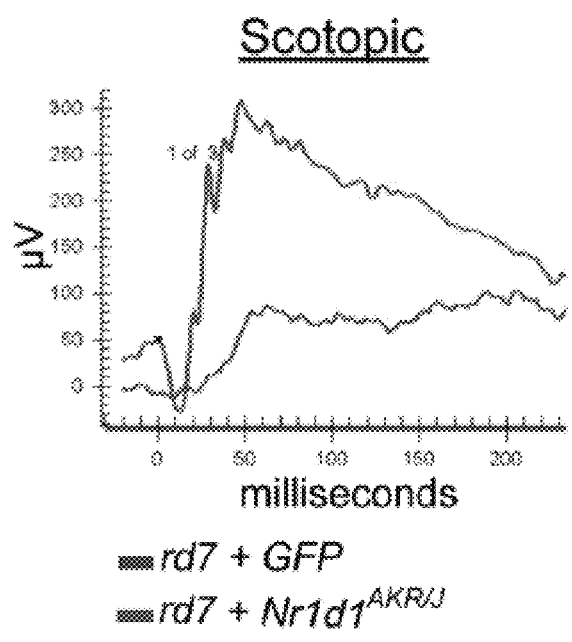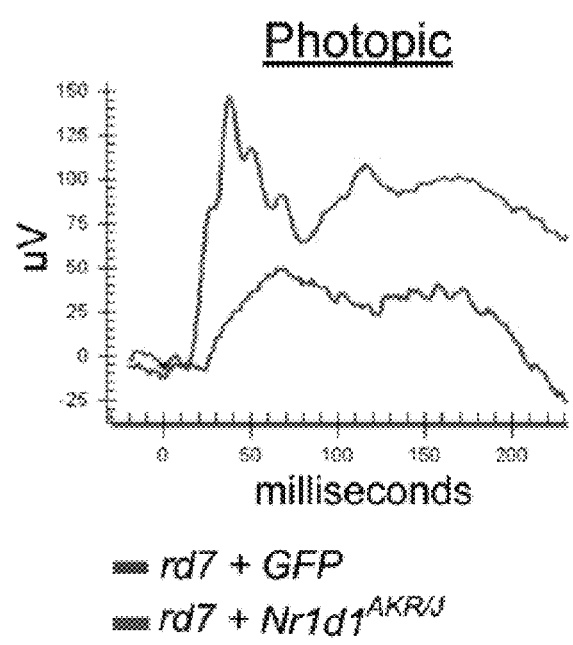
FIG. 3K
FIG. 3L

- A/B: AF-1 domain
- C: DBD
- D: variable hinge
- E: LBD, AF-2, dimerization domain, nuclear localization
- F: variable, nonfunctional (not present)

SEQUENCE LISTING

<160> NUMBER OF SEQ ID NOS: 29

<210> SEQ ID NO 1
<211> LENGTH: 34
<212> TYPE: DNA
<213> ORGANISM: Artificial Sequence
<220> FEATURE:
<223> OTHER INFORMATION: Chemically synthesized primer

<400> SEQUENCE: 1
tttttaagct tcatcacaac ctccagtttg tgtc                              34

<210> SEQ ID NO 2
<211> LENGTH: 34
<212> TYPE: DNA
<213> ORGANISM: Artificial Sequence
<220> FEATURE:
<223> OTHER INFORMATION: Chemically synthesized primer

<400> SEQUENCE: 2
tttttaagct tggcgtccac ccggaaggac agca                                34

<210> SEQ ID NO 3
<211> LENGTH: 34
<212> TYPE: DNA
<213> ORGANISM: Artificial Sequence
<220> FEATURE:
<223> OTHER INFORMATION: Chemically synthesized primer

<400> SEQUENCE: 3
tttttaagct tgcaagcagg ctacccttag gacc                                34

<210> SEQ ID NO 4
<211> LENGTH: 34
<212> TYPE: DNA
<213> ORGANISM: Artificial Sequence
<220> FEATURE:
<223> OTHER INFORMATION: Chemically synthesized primer

<400> SEQUENCE: 4
tttttaagct tgaacatgtc acacaggagc ttct                                34

<210> SEQ ID NO 5
<211> LENGTH: 1845
<212> TYPE: DNA
<213> ORGANISM: Homo sapiens

<400> SEQUENCE: 5
atgacgaccc tggactccaa caacaacaca ggtggcgtca tcacctacat tggctccagt    60
ggctcctccc caagccgcac cagccctgaa tccctctata gtgacaactc caatggcagc    120
ttccagtccc tgacccaagg ctgtcccacc tacttcccac catcccccac tggctccctc    180
acccaagacc cggctcgctc ctttgggagc attccaccca gcctgagtga tgacggctcc    240
ccttcttcct catcttcctc gtcgtcatcc tcctcctcct tctataatgg agccccccct    300
gggagtctac aagtggccat ggaggacagc agccgagtgt ccccagcaa gagcaccagc    360 aacatcacca agctgaatgg catggtgtta ctgtgtaaag tgtgtgggga cgttgcctcg    420
ggcttccact acggtgtgca cgcctgcgag ggctgcaagg cttttttccg tcggagcatc    480
cagcagaaca tccagtacaa aaggtgtctg aagaatgaga attgctccat cgtccgcatc    540
aatcgcaacc gctgccagca atgtcgcttc aagaagtgtc tctctgtggg catgtctcga    600
gacgctgtgc gttttgggcg catccccaaa cgagagaagc agcggatgct gctgagatg    660 cagagtgcca tgaacctggc caacaaccag ttgagcagcc agtgcccgct ggagacttca    720
cccacccagc accccacccc aggccccatg ggccctcgc cacccctgc tccggtcccc    780 tcaccctgg tgggcttctc ccagtttcca aacagctga cgcctcccag atccccaagc    840
cctgagccca cagtggagga tgtgatatcc caggtggccc gggcccatcg agagatcttc    900
acctacgccc atgacaagct gggcagctca cctggcaact tcaatgccaa ccatgcatca    960 ggtagcctc cagccaccac cccacatcgc tgggaaaatc agggctgccc acctgccccc    1020

```
aatgacaaca acaccttggc tgcccagcgt cataacgagg ccctaaatgg tctgcgccag    1080
gctccctcct cctaccctcc cacctggcct cctggccctg cacaccacag ctgccaccag    1140
tccaacagca acgggcaccg tctatgcccc acccacgtgt atgcagcccc agaaggcaag    1200
gcacctgcca acagtccccg cagggcaac tcaaagaatg ttctgctggc atgtcctatg     1260
aacatgtacc cgcatggacg cagtgggcga acggtgcagg agatctggga ggatttctcc    1320
atgagcttca cgcccgctgt gcgggaggtg gtagagtttg ccaaacacat cccgggcttc    1380
cgtgaccttt ctcagcatga ccaagtcacc ctgcttaagg ctggcacctt tgaggtgctg    1440
atggtgcgct ttgcttcgtt gttcaacgtg aaggaccaga cagtgatgtt cctaagccgc    1500
accacctaca gcctgcagga gcttggtgcc atgggcatgg agacctgctc agtgccatg    1560 ttcgacttca gcgagaagct caactccctg gcgcttaccg aggaggagct gggcctcttc    1620
accgcggtgg tgcttgtctc tgcagaccgc tcgggcatgg agaattccgc ttcggtggag    1680
cagctccagg agacgctgct gcgggctctt cgggctctgg tgctgaagaa ccggcccttg    1740
gagacttccc gcttcaccaa gctgctgctc aagctgccgg acctgcggac cctgaacaac    1800
atgcattccg agaagctgct gtccttccgg gtggacgccc agtga                    1845
```

<210> SEQ ID NO 6  
<211> LENGTH: 614  
<212> TYPE: PRT  
<213> ORGANISM: Homo sapiens

<400> SEQUENCE: 6

```
Met Thr Thr Leu Asp Ser Asn Asn Thr Gly Gly Val Ile Thr Tyr
1               5                   10                  15

Ile Gly Ser Ser Gly Ser Ser Pro Ser Arg Thr Ser Pro Glu Ser Leu
            20                  25                  30

Tyr Ser Asp Asn Ser Asn Gly Ser Phe Gln Ser Leu Thr Gln Gly Cys
        35                  40                  45

Pro Thr Tyr Phe Pro Pro Ser Pro Thr Gly Ser Leu Thr Gln Asp Pro
    50                  55                  60

Ala Arg Ser Phe Gly Ser Ile Pro Pro Ser Leu Ser Asp Asp Gly Ser
65                  70                  75                  80

Pro Ser Ser Ser Ser Ser Ser Ser Ser Ser Ser Phe Tyr Asn
                85                  90                  95

Gly Ser Pro Pro Gly Ser Leu Gln Val Ala Met Glu Asp Ser Ser Arg
            100                 105                 110

Val Ser Pro Ser Lys Ser Thr Ser Asn Ile Thr Lys Leu Asn Gly Met
        115                 120                 125

Val Leu Leu Cys Lys Val Cys Gly Asp Val Ala Ser Gly Phe His Tyr
    130                 135                 140

Gly Val His Ala Cys Glu Gly Cys Lys Gly Phe Phe Arg Arg Ser Ile
145                 150                 155                 160

Gln Gln Asn Ile Gln Tyr Lys Arg Cys Leu Lys Asn Glu Asn Cys Ser
                165                 170                 175

Ile Val Arg Ile Asn Arg Asn Arg Cys Gln Gln Cys Arg Phe Lys Lys
            180                 185                 190

Cys Leu Ser Val Gly Met Ser Arg Asp Ala Val Arg Phe Gly Arg Ile
        195                 200                 205

Pro Lys Arg Glu Lys Gln Arg Met Leu Ala Glu Met Gln Ser Ala Met
    210                 215                 220

Asn Leu Ala Asn Asn Gln Leu Ser Ser Gln Cys Pro Leu Glu Thr Ser
```

```
            225                 230                 235                 240
        Pro Thr Gln His Pro Thr Pro Gly Pro Met Gly Pro Ser Pro Pro Pro
                        245                 250                 255

Ala Pro Val Pro Ser Pro Leu Val Gly Phe Ser Gln Phe Pro Gln Gln
                    260                 265                 270

Leu Thr Pro Pro Arg Ser Pro Ser Pro Glu Pro Thr Val Glu Asp Val
                    275                 280                 285

Ile Ser Gln Val Ala Arg Ala His Arg Glu Ile Phe Thr Tyr Ala His
                290                 295                 300

Asp Lys Leu Gly Ser Ser Pro Gly Asn Phe Asn Ala Asn His Ala Ser
        305                 310                 315                 320

Gly Ser Pro Pro Ala Thr Thr Pro His Arg Trp Glu Asn Gln Gly Cys
                        325                 330                 335

Pro Pro Ala Pro Asn Asp Asn Asn Thr Leu Ala Ala Gln Arg His Asn
                    340                 345                 350

Glu Ala Leu Asn Gly Leu Arg Gln Ala Pro Ser Ser Tyr Pro Pro Thr
                    355                 360                 365

Trp Pro Pro Gly Pro Ala His His Ser Cys His Gln Ser Asn Ser Asn
                370                 375                 380

Gly His Arg Leu Cys Pro Thr His Val Tyr Ala Ala Pro Glu Gly Lys
        385                 390                 395                 400

Ala Pro Ala Asn Ser Pro Arg Gln Gly Asn Ser Lys Asn Val Leu Leu
                        405                 410                 415

Ala Cys Pro Met Asn Met Tyr Pro His Gly Arg Ser Gly Arg Thr Val
                    420                 425                 430

Gln Glu Ile Trp Glu Asp Phe Ser Met Ser Phe Thr Pro Ala Val Arg
                    435                 440                 445

Glu Val Val Glu Phe Ala Lys His Ile Pro Gly Phe Arg Asp Leu Ser
                450                 455                 460

Gln His Asp Gln Val Thr Leu Leu Lys Ala Gly Thr Phe Glu Val Leu
        465                 470                 475                 480

Met Val Arg Phe Ala Ser Leu Phe Asn Val Lys Asp Gln Thr Val Met
                        485                 490                 495

Phe Leu Ser Arg Thr Thr Tyr Ser Leu Gln Glu Leu Gly Ala Met Gly
                    500                 505                 510

Met Gly Asp Leu Leu Ser Ala Met Phe Asp Phe Ser Glu Lys Leu Asn
                    515                 520                 525

Ser Leu Ala Leu Thr Glu Glu Leu Gly Leu Phe Thr Ala Val Val
                530                 535                 540

Leu Val Ser Ala Asp Arg Ser Gly Met Glu Asn Ser Ala Ser Val Glu
        545                 550                 555                 560

Gln Leu Gln Glu Thr Leu Leu Arg Ala Leu Arg Ala Leu Val Leu Lys
                        565                 570                 575

Asn Arg Pro Leu Glu Thr Ser Arg Phe Thr Lys Leu Leu Leu Lys Leu
                    580                 585                 590

Pro Asp Leu Arg Thr Leu Asn Asn Met His Ser Glu Lys Leu Leu Ser
                    595                 600                 605

Phe Arg Val Asp Ala Gln
            610

<210> SEQ ID NO 7
<211> LENGTH: 2019
<212> TYPE: DNA
<213> ORGANISM: Homo sapiens
```

<400> SEQUENCE: 7

| | | | | | |
|---|---|---|---|---|---|
| ctcagcagca | gagttaagta | gtattgcttt | aattgcaaca | agctgagcta | atgtgggaag | 60 |
| aatgcagtag | agtggcacag | aagaatgcta | acccgaaact | ctaagcctgt | tccctggaat | 120 |
| cttccatctg | gatggaggag | agaaagttga | cctggagtga | ggttcaatgt | aaggacaaga | 180 |
| tctgcacccg | gagaagctct | ctctcggaga | gcacaggcgg | cctgaggagt | caaaacaggt | 240 |
| ggcctgtgga | gtcagcacag | gcagcctgga | ggaggtgagg | aactgaagtt | tggacagatt | 300 |
| gagtcacttt | ctcagggaca | catggctggc | cggtgatgga | gaaggcgtga | gcccctcgct | 360 |
| ccagtgccgc | gtgtgcggag | acagcagcag | cgggaagcac | tatggcatct | atgcctgcaa | 420 |
| cggctgcagc | ggcttcttca | gaggagcgt | acggcggagg | ctcatctaca | ggtgccaggt | 480 |
| gggggcaggg | atgtgccccg | tggacaaggc | ccaccgcaac | cagtgccagg | cctgccggct | 540 |
| gaagaagtgc | ctgcaggcgg | ggatgaacca | ggacgccgtg | cagaacgagc | gccagccgcg | 600 |
| aagcacagcc | caggtccacc | tggacagcat | ggagtccaac | actgagtccc | ggccggagtc | 660 |
| cctggtggct | cccccggccc | cggcagggcg | cagcccacgg | ggccccacac | ccatgtctgc | 720 |
| agccagagcc | ctgggccacc | acttcatggc | cagcctttata | acagctgaaa | cctgtgctaa | 780 |
| gctggagcca | gaggatgctg | atgagaatat | tgatgtcacc | agcaatgacc | ctgagttccc | 840 |
| ctcctctcca | tactcctctt | cctcccccctg | cggcctggac | agcatccatg | agacctcggc | 900 |
| tcgcctactc | ttcatggccg | tcaagtgggc | caagaacctg | cctgtgttct | ccagcctgcc | 960 |
| cttccgggat | caggtgatcc | tgctggaaga | ggcgtggagt | gaactctttc | tcctcggggc | 1020 |
| catccagtgg | tctctgcctc | tggacagctg | tcctctgctg | gcaccgcccg | aggcctctgc | 1080 |
| tgccggtggt | gcccagggcc | ggctcacgct | ggccagcatg | gagacgcgtg | tcctgcagga | 1140 |
| aactatctct | cggttccggg | cattggcggt | ggaccccacg | gagtttgcct | gcatgaaggc | 1200 |
| cttggtcctc | ttcaagccag | agacgcgggg | cctgaaggat | cctgagcacg | tagaggcctt | 1260 |
| gcaggaccag | tcccaagtga | tgctgagcca | gcacagcaag | gcccaccacc | ccagccagcc | 1320 |
| cgtgaggttt | gggaaattgc | tcctgctcct | cccgtctttg | aggtttatca | ctgcggaacg | 1380 |
| catcgagctc | ctcttttttcc | gcaagaccat | agggaatact | ccaatggaga | agctccttttg | 1440 |
| tgatatgttc | aaaaactagt | gggggtggag | gtgaaatgtt | tccaagcact | ctggaaaaca | 1500 |
| atctactgaa | acgaaacatt | tgcctactct | ttgccccagc | aattcctcgt | aggtgtgtgt | 1560 |
| acccagcaga | aatgcccacc | gaaagatatt | gtaagaatat | tcatagcagc | tttattcata | 1620 |
| atagccccaa | actgtatatt | gatggtagga | tgaattaaca | agttgtggta | tattcatata | 1680 |
| atgaaaaata | atttaaaaag | aatgaattac | ggatacatgt | ggcaacacag | gtaaacttca | 1740 |
| cagacataaa | agttgaatga | agaagccag | gccgaagttc | catttatgca | gagttcagga | 1800 |
| acaggcaaga | ctaattgaca | ataatagaag | ttggaatagt | ggttacttct | gggtggtggg | 1860 |
| ggattgatac | agaggggggct | catgggagcc | ctctggtgta | ccagaaatgt | tgattttgat | 1920 |
| ctgggcagtg | gtttcacaaa | tgtattcata | cgtaataatt | cattgagctg | tgcactttat | 1980 |
| tttgttagac | ctcaataaaa | aagtaaaaaa | aaaaaaaaa | | | 2019 |

<210> SEQ ID NO 8
<211> LENGTH: 322
<212> TYPE: PRT
<213> ORGANISM: Homo sapiens

<400> SEQUENCE: 8

```
Met Cys Pro Val Asp Lys Ala His Arg Asn Gln Cys Gln Ala Cys Arg
1               5                   10                  15
Leu Lys Lys Cys Leu Gln Ala Gly Met Asn Gln Asp Ala Val Gln Asn
            20                  25                  30
Glu Arg Gln Pro Arg Ser Thr Ala Gln Val His Leu Asp Ser Met Glu
        35                  40                  45
Ser Asn Thr Glu Ser Arg Pro Glu Ser Leu Val Ala Pro Pro Ala Pro
50                  55                  60
Ala Gly Arg Ser Pro Arg Gly Pro Thr Pro Met Ser Ala Ala Arg Ala
65                  70                  75                  80
Leu Gly His His Phe Met Ala Ser Leu Ile Thr Ala Glu Thr Cys Ala
                85                  90                  95
Lys Leu Glu Pro Glu Asp Ala Asp Glu Asn Ile Asp Val Thr Ser Asn
            100                 105                 110
Asp Pro Glu Phe Pro Ser Ser Pro Tyr Ser Ser Ser Pro Cys Gly
        115                 120                 125
Leu Asp Ser Ile His Glu Thr Ser Ala Arg Leu Leu Phe Met Ala Val
130                 135                 140
Lys Trp Ala Lys Asn Leu Pro Val Phe Ser Ser Leu Pro Phe Arg Asp
145                 150                 155                 160
Gln Val Ile Leu Leu Glu Glu Ala Trp Ser Glu Leu Phe Leu Leu Gly
                165                 170                 175
Ala Ile Gln Trp Ser Leu Pro Leu Asp Ser Cys Pro Leu Leu Ala Pro
            180                 185                 190
Pro Glu Ala Ser Ala Ala Gly Gly Ala Gln Gly Arg Leu Thr Leu Ala
        195                 200                 205
Ser Met Glu Thr Arg Val Leu Gln Glu Thr Ile Ser Arg Phe Arg Ala
210                 215                 220
Leu Ala Val Asp Pro Thr Glu Phe Ala Cys Met Lys Ala Leu Val Leu
225                 230                 235                 240
Phe Lys Pro Glu Thr Arg Gly Leu Lys Asp Pro Glu His Val Glu Ala
                245                 250                 255
Leu Gln Asp Gln Ser Gln Val Met Leu Ser Gln His Ser Lys Ala His
            260                 265                 270
His Pro Ser Gln Pro Val Arg Phe Gly Lys Leu Leu Leu Leu Pro
        275                 280                 285
Ser Leu Arg Phe Ile Thr Ala Glu Arg Ile Glu Leu Leu Phe Phe Arg
290                 295                 300
Lys Thr Ile Gly Asn Thr Pro Met Glu Lys Leu Leu Cys Asp Met Phe
305                 310                 315                 320
Lys Asn

<210> SEQ ID NO 9
<211> LENGTH: 1950
<212> TYPE: DNA
<213> ORGANISM: Homo sapiens

<400> SEQUENCE: 9
ccatctgtct gatcaccttg gactccatag tacactgggg caaagcacag ccccagtttc     60
tggaggcaga tgggtaacca ggaaaaggca tgaatgaggg ggccccagga gacagtgact    120
tagagactga ggcaagagtg ccgtggtcaa tcatgggtca ttgtcttcga actggacagg    180
ccagaatgtc tgccacaccc acacctgcag gtgaaggagc cagaagggat gaactttttg    240
ggattctcca aatactccat cagtgtatcc tgtcttcagg tgatgctttt gttcttactg    300
```

```
gcgtctgttg ttcctggagg cagaatggca agccaccata ttcacaaaag gaagataagg    360
aagtacaaac tggatacatg aatgctcaaa ttgaaattat tccatgcaag atctgtggag    420
acaaatcatc aggaatccat tatggtgtca ttacatgtga aggctgcaag ggcttttttca   480 ggagaagtca gcaaagcaat gccacctact cctgtcctcg tcagaagaac tgtttgattg    540
atcgaaccag tagaaaccgc tgccaacact gtcgattaca gaaatgcctt gccgtaggga    600
tgtctcgaga tgctgtaaaa tttggccgaa tgtcaaaaaa gcagagagac agcttgtatg    660
cagaagtaca gaaacaccgg atgcagcagc agcagcgcga ccaccagcag cagcctggag    720
aggctgagcc gctgacgccc acctacaaca tctcggccaa cgggctgacg gaacttcacg    780
acgacctcag taactacatt gacgggcaca cccctgaggg gagtaaggca gactccgccg    840
tcagcagctt ctacctggac atacagcctt cccagacca gtcaggtctt gatatcaatg    900
gaatcaaacc agaaccaata tgtgactaca caccagcatc aggcttcttt ccctactgtt    960
cgttcaccaa cggcgagact tccccaactg tgtccatggc agaattagaa cacctttgcac   1020 agaatatatc taaatcgcat ctggaaacct gccaatactt gagagaagag ctccagcaga    1080
taacgtggca gaccttttta caggaagaaa ttgagaacta tcaaaacaag cagcgggagg    1140
tgatgtggca attgtgtgcc atcaaaatta cagaagctat acagtatgtg gtggagtttg    1200
ccaaacgcat tgatggattt atggaactgt gtcaaaatga tcaaattgtg cttctaaaag    1260
caggttctct agaggtggtg tttatcagaa tgtgccgtgc ctttgactct cagaacaaca    1320
ccgtgtactt tgatgggaag tatgccagcc ccgacgtctt caaatcctta ggttgtgaag    1380
actttattag ctttgtgttt gaatttggaa agagtttatg ttctatgcac ctgactgaag    1440
atgaaattgc attattttct gcatttgtac tgatgtcagc agatcgctca tggctgcaag    1500
aaaaggtaaa aattgaaaaa ctgcaacaga aaattcagct agctcttcaa cacgtcctac    1560
agaagaatca ccgagaagat ggaatactaa caaagttaat atgcaaggtg tctacattaa    1620
gagccttatg tggacgacat acagaaaagc taatggcatt taaagcaata tacccagaca    1680
ttgtgcgact tcattttcct ccattataca aggagttgtt cacttcagaa tttgagccag    1740
caatgcaaat tgatgggtaa atgttatcac ctaagcactt ctagaatgtc tgaagtacaa    1800
acatgaaaaa caaacaaaaa aattaaccga gacactttat atggccctgc acagacctgg    1860
agcgccacac actgcacatc ttttggtgat cggggtcagg caaaggaggg gaaacaatga    1920
aaacaaataa agttgaactt gtttttctca                                     1950
```

<210> SEQ ID NO 10
<211> LENGTH: 556
<212> TYPE: PRT
<213> ORGANISM: Homo sapiens

<400> SEQUENCE: 10

```
Met Asn Glu Gly Ala Pro Gly Asp Ser Asp Leu Glu Thr Glu Ala Arg
1               5                   10                  15

Val Pro Trp Ser Ile Met Gly His Cys Leu Arg Thr Gly Gln Ala Arg
            20                  25                  30

Met Ser Ala Thr Pro Thr Pro Ala Gly Glu Gly Ala Arg Arg Asp Glu
        35                  40                  45

Leu Phe Gly Ile Leu Gln Ile Leu His Gln Cys Ile Leu Ser Ser Gly
    50                  55                  60

Asp Ala Phe Val Leu Thr Gly Val Cys Cys Ser Trp Arg Gln Asn Gly
65                  70                  75                  80
```

```
Lys Pro Pro Tyr Ser Gln Lys Glu Asp Lys Glu Val Gln Thr Gly Tyr
                85                  90                  95

Met Asn Ala Gln Ile Glu Ile Ile Pro Cys Lys Ile Cys Gly Asp Lys
            100                 105                 110

Ser Ser Gly Ile His Tyr Gly Val Ile Thr Cys Glu Gly Cys Lys Gly
            115                 120                 125

Phe Phe Arg Arg Ser Gln Gln Ser Asn Ala Thr Tyr Ser Cys Pro Arg
    130                 135                 140

Gln Lys Asn Cys Leu Ile Asp Arg Thr Ser Arg Asn Arg Cys Gln His
145                 150                 155                 160

Cys Arg Leu Gln Lys Cys Leu Ala Val Gly Met Ser Arg Asp Ala Val
                165                 170                 175

Lys Phe Gly Arg Met Ser Lys Lys Gln Arg Asp Ser Leu Tyr Ala Glu
            180                 185                 190

Val Gln Lys His Arg Met Gln Gln Gln Arg Asp His Gln Gln Gln
            195                 200                 205

Pro Gly Glu Ala Glu Pro Leu Thr Pro Thr Tyr Asn Ile Ser Ala Asn
    210                 215                 220

Gly Leu Thr Glu Leu His Asp Asp Leu Ser Asn Tyr Ile Asp Gly His
225                 230                 235                 240

Thr Pro Glu Gly Ser Lys Ala Asp Ser Ala Val Ser Ser Phe Tyr Leu
                245                 250                 255

Asp Ile Gln Pro Ser Pro Asp Gln Ser Gly Leu Asp Ile Asn Gly Ile
            260                 265                 270

Lys Pro Glu Pro Ile Cys Asp Tyr Thr Pro Ala Ser Gly Phe Phe Pro
            275                 280                 285

Tyr Cys Ser Phe Thr Asn Gly Glu Thr Ser Pro Thr Val Ser Met Ala
    290                 295                 300

Glu Leu Glu His Leu Ala Gln Asn Ile Ser Lys Ser His Leu Glu Thr
305                 310                 315                 320

Cys Gln Tyr Leu Arg Glu Glu Leu Gln Gln Ile Thr Trp Gln Thr Phe
                325                 330                 335

Leu Gln Glu Glu Ile Glu Asn Tyr Gln Asn Lys Gln Arg Glu Val Met
            340                 345                 350

Trp Gln Leu Cys Ala Ile Lys Ile Thr Glu Ala Ile Gln Tyr Val Val
            355                 360                 365

Glu Phe Ala Lys Arg Ile Asp Gly Phe Met Glu Leu Cys Gln Asn Asp
    370                 375                 380

Gln Ile Val Leu Leu Lys Ala Gly Ser Leu Glu Val Val Phe Ile Arg
385                 390                 395                 400

Met Cys Arg Ala Phe Asp Ser Gln Asn Asn Thr Val Tyr Phe Asp Gly
                405                 410                 415

Lys Tyr Ala Ser Pro Asp Val Phe Lys Ser Leu Gly Cys Glu Asp Phe
            420                 425                 430

Ile Ser Phe Val Phe Glu Phe Gly Lys Ser Leu Cys Ser Met His Leu
            435                 440                 445

Thr Glu Asp Glu Ile Ala Leu Phe Ser Ala Phe Val Leu Met Ser Ala
    450                 455                 460

Asp Arg Ser Trp Leu Gln Glu Lys Val Lys Ile Glu Lys Leu Gln Gln
465                 470                 475                 480

Lys Ile Gln Leu Ala Leu Gln His Val Leu Gln Lys Asn His Arg Glu
                485                 490                 495
```

Asp Gly Ile Leu Thr Lys Leu Ile Cys Lys Val Ser Thr Leu Arg Ala
            500                 505                 510

Leu Cys Gly Arg His Thr Glu Lys Leu Met Ala Phe Lys Ala Ile Tyr
        515                 520                 525

Pro Asp Ile Val Arg Leu His Phe Pro Pro Leu Tyr Lys Glu Leu Phe
    530                 535                 540

Thr Ser Glu Phe Glu Pro Ala Met Gln Ile Asp Gly
545                 550                 555

<210> SEQ ID NO 11
<211> LENGTH: 2147
<212> TYPE: DNA
<213> ORGANISM: Homo sapiens

<400> SEQUENCE: 11

| | | | | |
|---|---|---|---|---|
| gcttctcccc | gttgctaatg | cgcaggcgct | ggcgggatag | cgcgccgccg | agccgagaaa | 60 |
| gaggtcacga | actctgaccc | cccagaaata | cccaaacaca | gaaagctctc | tccgccgtga | 120 |
| atctcgatcc | cacatcccgt | cggctttctt | caacctctct | tcccggagcg | cccccccaatc | 180 |
| cacgagtggc | agccgcggga | ctgtcgcgtc | ggcgcccgac | gccggagtca | gcagggcgca | 240 |
| aaagcgccgg | tagatcatgg | caaccataga | agaaattgca | catcaaatta | ttgaacaaca | 300 |
| gatgggagag | attgttacag | agcagcaaac | tgggcagaaa | atccagattg | tgacagcact | 360 |
| tgatcataat | acccaaggca | agcagttcat | tctgacaaat | cacgacggct | ctactccaag | 420 |
| caaagtcatt | ctggccaggc | aagattccac | tccgggaaaa | gttttcctta | caactccaga | 480 |
| tgcagcaggt | gtcaaccagt | tattttttac | cactcctgat | ctgtctgcac | aacacctgca | 540 |
| gctcctaaca | gataattctc | cagaccaagg | accaaataag | gttttttgatc | tttgcgtagt | 600 |
| atgtggagac | aaagcatcag | gacgtcatta | tggagcagta | acttgtgaag | gctgcaaagg | 660 |
| attttttaaa | agaagcatcc | gaaaaaattt | agtatattca | tgtcgaggat | caaggattg | 720 |
| tattattaat | aagcaccacc | gaaaccgctg | tcaatactgc | aggttacaga | gatgtattgc | 780 |
| gtttggaatg | aagcaagact | ctgtccaatg | tgaaagaaaa | cccattgaag | tatcacgaga | 840 |
| aaaatcttcc | aactgtgccg | cttcaacaga | aaaaatctat | atccgaaagg | accttcgtag | 900 |
| cccattaact | gcaactccaa | cttttgtaac | agatagtgaa | agtacaaggt | caacaggact | 960 |
| gttagattca | ggaatgttca | tgaatattca | tccatctgga | gtaaaaactg | agtcagctgt | 1020 |
| gctgatgaca | tcagataagg | ctgaatcatg | tcagggagat | ttaagtacat | ggccaatgt | 1080 |
| ggttacatca | ttagcgaatc | ttggaaaaac | taaagatctt | tctcaaaata | gtaatgaaat | 1140 |
| gtctatgatt | gaaagcttaa | gcaatgatga | tacctctttg | tgtgaatttc | aagaaatgca | 1200 |
| gaccaacggt | gatgtttcaa | gggcatttga | cactcttgca | aaagcattga | atcctggaga | 1260 |
| gagcacagcc | tgccagagct | cagtagcggg | catggaagga | agtgtacacc | taatcactgg | 1320 |
| agattcaagc | ataaattaca | ccgaaaaaga | ggggccactt | ctcagcgatt | cacatgtagc | 1380 |
| tttcaggctc | accatgcctt | ctcctatgcc | tgagtacctg | aatgtgcact | acattgggga | 1440 |
| gtctgcctcc | agactgctgt | tcttatcaat | gcactgggca | ctttcgattc | cttctttcca | 1500 |
| ggctctaggg | caagaaaaca | gcatatcact | ggtgaaagct | tactgaatg | aacttttac | 1560 |
| tcttggtctt | gcccagtgct | ggcaagtgat | gaatgtagca | actatattag | caacatttgt | 1620 |
| caattgtctt | cacaatagtc | ttcaacaaga | tgccaaggta | attgcagccc | tcattcattt | 1680 |
| cacaagacga | gcaatcactg | atttataaat | gcttaactat | agaatggctt | atgactaccc | 1740 |
| aaaacagtgc | cccatcaaca | aatggggaaa | attgccttttt | gagctcagga | ataatttata | 1800 |

-continued

```
aattggggac tacctttag ttctttagca tattctattt cttattgttt tatataattt   1860
ttaaatcatt tgcttcctcc ttatgtttaa cagcagaggg gtaatcacct taaaatgtca   1920
tcaaaaatag atctactaga aggcagcatc acattcccat cttacttatg gactcctacc   1980
cctggttcat gtcttatatg cctgtaatgg ttataaagcc taccttcagg aaagctatgg   2040
ttgactaatt actaatggat gggttttaaa catgtccctc tacaataaat taaaatcttt   2100
attgtaaaac tttaaaaaaa aaaaaaaaaa aaaaaaaaa aaaaaaa                   2147
```

<210> SEQ ID NO 12
<211> LENGTH: 603
<212> TYPE: PRT
<213> ORGANISM: Homo sapiens

<400> SEQUENCE: 12

```
Met Ala Thr Ile Glu Glu Ile Ala His Gln Ile Ile Glu Gln Gln Met
1               5                   10                  15

Gly Glu Ile Val Thr Glu Gln Gln Thr Gly Gln Lys Ile Gln Ile Val
            20                  25                  30

Thr Ala Leu Asp His Asn Thr Gln Gly Lys Gln Phe Ile Leu Thr Asn
        35                  40                  45

His Asp Gly Ser Thr Pro Ser Lys Val Ile Leu Ala Arg Gln Asp Ser
    50                  55                  60

Thr Pro Gly Lys Val Phe Leu Thr Thr Pro Asp Ala Ala Gly Val Asn
65                  70                  75                  80

Gln Leu Phe Phe Thr Thr Pro Asp Leu Ser Ala Gln His Leu Gln Leu
                85                  90                  95

Leu Thr Asp Asn Ser Pro Asp Gln Gly Pro Asn Lys Val Phe Asp Leu
            100                 105                 110

Cys Val Val Cys Gly Asp Lys Ala Ser Gly Arg His Tyr Gly Ala Val
        115                 120                 125

Thr Cys Glu Gly Cys Lys Gly Phe Phe Lys Arg Ser Ile Arg Lys Asn
    130                 135                 140

Leu Val Tyr Ser Cys Arg Gly Ser Lys Asp Cys Ile Ile Asn Lys His
145                 150                 155                 160

His Arg Asn Arg Cys Gln Tyr Cys Arg Leu Gln Arg Cys Ile Ala Phe
                165                 170                 175

Gly Met Lys Gln Asp Ser Val Gln Cys Glu Arg Lys Pro Ile Glu Val
            180                 185                 190

Ser Arg Glu Lys Ser Ser Asn Cys Ala Ala Ser Thr Glu Lys Ile Tyr
        195                 200                 205

Ile Arg Lys Asp Leu Arg Ser Pro Leu Thr Ala Thr Pro Thr Phe Val
    210                 215                 220

Thr Asp Ser Glu Ser Thr Arg Ser Thr Gly Leu Leu Asp Ser Gly Met
225                 230                 235                 240

Phe Met Asn Ile His Pro Ser Gly Val Lys Thr Glu Ser Ala Val Leu
                245                 250                 255

Met Thr Ser Asp Lys Ala Glu Ser Cys Gln Gly Asp Leu Ser Thr Leu
            260                 265                 270

Ala Asn Val Val Thr Ser Leu Ala Asn Leu Gly Lys Thr Lys Asp Leu
        275                 280                 285

Ser Gln Asn Ser Asn Glu Met Ser Met Ile Glu Ser Leu Ser Asn Asp
    290                 295                 300

Asp Thr Ser Leu Cys Glu Phe Gln Glu Met Gln Thr Asn Gly Asp Val
```

```
                305                 310                 315                 320
Ser Arg Ala Phe Asp Thr Leu Ala Lys Ala Leu Asn Pro Gly Glu Ser
                325                 330                 335
Thr Ala Cys Gln Ser Ser Val Ala Gly Met Glu Gly Ser Val His Leu
                340                 345                 350
Ile Thr Gly Asp Ser Ser Ile Asn Tyr Thr Glu Lys Glu Gly Pro Leu
                355                 360                 365
Leu Ser Asp Ser His Val Ala Phe Arg Leu Thr Met Pro Ser Pro Met
                370                 375                 380
Pro Glu Tyr Leu Asn Val His Tyr Ile Gly Glu Ser Ala Ser Arg Leu
385                 390                 395                 400
Leu Phe Leu Ser Met His Trp Ala Leu Ser Ile Pro Ser Phe Gln Ala
                405                 410                 415
Leu Gly Gln Glu Asn Ser Ile Ser Leu Val Lys Ala Tyr Trp Asn Glu
                420                 425                 430
Leu Phe Thr Leu Gly Leu Ala Gln Cys Trp Gln Val Met Asn Val Ala
                435                 440                 445
Thr Ile Leu Ala Thr Phe Val Asn Cys Leu His Asn Ser Leu Gln Gln
                450                 455                 460
Asp Lys Met Ser Thr Glu Arg Arg Lys Leu Leu Met Glu His Ile Phe
465                 470                 475                 480
Lys Leu Gln Glu Phe Cys Asn Ser Met Val Lys Leu Cys Ile Asp Gly
                485                 490                 495
Tyr Glu Tyr Ala Tyr Leu Lys Ala Ile Val Leu Phe Ser Pro Asp His
                500                 505                 510
Pro Ser Leu Glu Asn Met Glu Leu Ile Glu Lys Phe Gln Glu Lys Ala
                515                 520                 525
Tyr Val Glu Phe Gln Asp Tyr Ile Thr Lys Thr Tyr Pro Asp Asp Thr
                530                 535                 540
Tyr Arg Leu Ser Arg Leu Leu Leu Arg Leu Pro Ala Leu Arg Leu Met
545                 550                 555                 560
Asn Ala Thr Ile Thr Glu Glu Leu Phe Phe Lys Gly Leu Ile Gly Asn
                565                 570                 575
Ile Arg Ile Asp Ser Val Ile Pro His Ile Leu Lys Met Glu Pro Ala
                580                 585                 590
Asp Tyr Asn Ser Gln Ile Ile Gly His Ser Ile
                595                 600

<210> SEQ ID NO 13
<211> LENGTH: 30
<212> TYPE: DNA
<213> ORGANISM: Homo sapiens

<400> SEQUENCE: 13
gagctccaga ttcgccaccc cgcagcgctg                                          30

<210> SEQ ID NO 14
<211> LENGTH: 30
<212> TYPE: DNA
<213> ORGANISM: Pan troglodytes

<400> SEQUENCE: 14
gagctccaga ttcgctaccc cgcagcgctg                                          30

<210> SEQ ID NO 15
<211> LENGTH: 30
```

```
<212> TYPE: DNA
<213> ORGANISM: Canis familiaris

<400> SEQUENCE: 15
gagctccaga ttcgctaccc tgcagcgctg                                    30

<210> SEQ ID NO 16
<211> LENGTH: 30
<212> TYPE: DNA
<213> ORGANISM: Bos primigenius

<400> SEQUENCE: 16
gagctccaga ttcgataccc tgcagcgctg                                    30

<210> SEQ ID NO 17
<211> LENGTH: 30
<212> TYPE: DNA
<213> ORGANISM: Mus musculus

<400> SEQUENCE: 17
gagctccaga ttcattaccc tgcttcactg                                    30

<210> SEQ ID NO 18
<211> LENGTH: 21
<212> TYPE: PRT
<213> ORGANISM: Mus musculus

<400> SEQUENCE: 18

Pro Glu Gly Glu Ala Pro Ala Asn Ser Leu Arg Gln Gly Asn Thr Lys
1               5                   10                  15

Asn Val Leu Leu Ala
            20

<210> SEQ ID NO 19
<211> LENGTH: 21
<212> TYPE: PRT
<213> ORGANISM: Mus musculus

<400> SEQUENCE: 19

Pro Glu Gly Glu Ala Pro Ala Asn Ser Leu Gln Gln Gly Asn Thr Lys
1               5                   10                  15

Asn Val Leu Leu Ala
            20

<210> SEQ ID NO 20
<211> LENGTH: 21
<212> TYPE: PRT
<213> ORGANISM: Rattus norvegicus

<400> SEQUENCE: 20

Pro Glu Gly Lys Ala Pro Ala Asn Gly Leu Arg Gln Gly Asn Thr Lys
1               5                   10                  15

Asn Val Leu Leu Ala
            20

<210> SEQ ID NO 21
<211> LENGTH: 21
<212> TYPE: PRT
<213> ORGANISM: Pan troglodytes

<400> SEQUENCE: 21

Pro Glu Gly Lys Ala Pro Ala Asn Ser Pro Arg Gln Gly Asn Ser Lys
1               5                   10                  15
```

Asn Val Leu Leu Ala
            20

<210> SEQ ID NO 22
<211> LENGTH: 21
<212> TYPE: PRT
<213> ORGANISM: Homo sapiens

<400> SEQUENCE: 22

Pro Glu Gly Lys Ala Pro Ala Asn Ser Pro Arg Gln Gly Asn Ser Lys
1               5                   10                  15

Asn Val Leu Leu Ala
            20

<210> SEQ ID NO 23
<211> LENGTH: 21
<212> TYPE: DNA
<213> ORGANISM: Mus musculus

<400> SEQUENCE: 23
aactgcgggg ctcactcgtc t                                            21

<210> SEQ ID NO 24
<211> LENGTH: 21
<212> TYPE: DNA
<213> ORGANISM: Mus musculus

<400> SEQUENCE: 24
aactgcgggg ttcactcgtc t                                            21

<210> SEQ ID NO 25
<211> LENGTH: 21
<212> TYPE: DNA
<213> ORGANISM: Rattus norvegicus

<400> SEQUENCE: 25
aactgcgggc ttcactcgtc t                                            21

<210> SEQ ID NO 26
<211> LENGTH: 21
<212> TYPE: DNA
<213> ORGANISM: Pan troglodytes

<400> SEQUENCE: 26
agtcgcgggg tccactcccc g                                            21

<210> SEQ ID NO 27
<211> LENGTH: 21
<212> TYPE: DNA
<213> ORGANISM: Homo sapiens

<400> SEQUENCE: 27
agtcgcgggg tccactcccc g                                            21

<210> SEQ ID NO 28
<211> LENGTH: 658
<212> TYPE: DNA
<213> ORGANISM: Homo sapiens

<400> SEQUENCE: 28
caaagcgtta ggagaagaag agaggcaggg aagacaagcc aggcacgatg gccaccttcc    60
caccagcaac cagcgccccc cagcagcccc caggcccgga ggacgaggac tccagcctgg   120

```
atgaatctga cctctatagc ctggcccatt cctacctcgg aggtggaggc cggaaaggtc    180
gcaccaagag agaagctgct gccaacacca accgccccag ccctggcggg cacgagagga    240
aactggtgac caagctgcag aattcagaga ggaagaagcg aggggcacgg cgctgagaca    300
gagctggaga tgaggccaga ccatggacac tacacccagc aatagagacg ggactgcgga    360
ggaaggagga cccaggacag gatccaggcc ggcttgccac acccccacc cctaggactt     420 attcccgctg actgagtctc tgaggggcta ccaggaaagc gcctccaacc ctagcaaaag    480
tgcaagatgg ggagtgagag gctgggaatg gaggggcaga gccaggaaga tcccccagaa    540
aagaaagcta cagaagaaac tggggctcct ccagggtggc agcaacaata aatagacacg    600
cacggcagcc acaaaaaaaa aaaaaaaaaa aaaaaaaaaa aaaaaaaaaa aaaaaaa       658
```

<210> SEQ ID NO 29
<211> LENGTH: 82
<212> TYPE: PRT
<213> ORGANISM: Homo sapiens

<400> SEQUENCE: 29

```
Met Ala Thr Phe Pro Pro Ala Thr Ser Ala Pro Gln Gln Pro Pro Gly
1               5                   10                  15

Pro Glu Asp Glu Asp Ser Ser Leu Asp Glu Ser Asp Leu Tyr Ser Leu
            20                  25                  30

Ala His Ser Tyr Leu Gly Gly Gly Arg Lys Gly Arg Thr Lys Arg
        35                  40                  45

Glu Ala Ala Asn Thr Asn Arg Pro Ser Pro Gly Gly His Glu Arg
    50                  55                  60

Lys Leu Val Thr Lys Leu Gln Asn Ser Glu Arg Lys Lys Arg Gly Ala
65                  70                  75                  80

Arg Arg
```

METHODS FOR MODULATING DEVELOPMENT AND FUNCTION OF PHOTORECEPTOR CELLS

RELATED APPLICATIONS

This application is a Continuation Application of U.S. patent application Ser. No. 14/772,039, filed Sep. 1, 2015, which is a national stage application, filed under 35 U.S.C. § 371, of International Application No. PCT/US2014/020038, filed on Mar. 3, 2014, which claims priority to U.S. Provisional Application No. 61/771,503 filed Mar. 1, 2013, the contents of which are hereby incorporated by reference in its entirety.

FEDERALLY SPONSORED RESEARCH OR DEVELOPMENT

This invention was made with Government support under Grant No. EY017653 awarded by the National Institute of Health and the National Eye Institute. The Government has certain rights in the invention.

INCORPORATION-BY-REFERENCE OF SEQUENCE LISTING

The contents of the text file named "36770_537C01US_ST25.txt", which was created on Nov. 17, 2017 and is 33.6 KB in size, are hereby incorporated by reference in their entireties.

FIELD OF THE DISCLOSURE

The present invention relates to compositions and methods for administering gene modifiers for treating ocular disease.

BACKGROUND OF THE DISCLOSURE

Genetic heterogeneity is observed for many Mendelian, single gene disorders. While environmental influences provide minor contributions, variations in phenotypic outcome are generally attributable to allelic heterogeneity or genetic modifier genes, allelic variants distinct from the mutant gene, which can affect disease onset, progression, and outcome by either increasing or reducing disease severity. As such, prior to the invention described herein, there was a pressing need to identify genetic modifiers of disease.

SUMMARY OF THE DISCLOSURE

The present invention relates to the delivery of compositions that modify or restore the signaling pathways and/or function of photoreceptors for use in the treatment and prevention of ocular diseases or disorders. For example, the invention provides for methods of treating or reducing the severity of an ocular disease or disorder in a subject in need thereof by locally administering to an ocular or adnexal tissue of the subject a composition comprising a nucleic acid comprising a nucleic acid encoding a nuclear hormone receptor or fragment thereof. The present invention further provides compositions comprising a nucleic acid encoding a nuclear hormone receptor or fragment thereof for local administration to the ocular or adnexal tissue of a subject for treating or reducing the severity of an ocular disease or disorder.

Preferably, the nuclear hormone receptor or fragment thereof increases the amount of photoreceptors, increases the activity of photoreceptors, or normalizes the activity of photoreceptors in an ocular cell. In some embodiments, the nucleic acid encodes Nr1d1, Nr2e3, Rora, Nupr1, Nr2C1, or a fragment thereof. The nuclear hormone receptors of the present invention regulate a level of a photopigment. Examples of photopigments include, but are not limited to rhodopsin, S-opsin, M-opsin, L-opsin, or L/M-opsin.

In some preferred embodiments, the nuclear hormone receptor includes a photoreceptor-specific nuclear hormone receptor. For example, photoreceptor-specific nuclear hormone receptor comprises Nr2e3.

The subject is preferably a mammal in need of such treatment, e.g., a subject that is suffering from or at risk of developing an ocular disease or disorder. The ocular disease or disorder is characterized by retinal degeneration, e.g., photoreceptor degeneration. Photoreceptor degeneration can be characterized by loss or death of photoreceptor cells, such as rod and cone cells in the retina. In one example, the ocular disease or disorder is characterized by Nr2e3-associated retinal degeneration. For example, the ocular disease or disorder is selected from enhanced S-cone syndrome (ESCS), Goldmann-Favre syndrome, age-related macular degeneration (AMD), retinitis pigmentosa (RP), including, among others, autosomal dominant retinitis pigmentosa.

Administration of the gene modifier ameliorates clinical, morphological, and functional defects associated with the primary gene mutation. Preferably, retinal integrity and visual function are restored in the subject. Additionally, the methods and compositions provided herein are useful for alleviating or reducing at least one symptom associated with the ocular disease or disorder. Symptoms include retinal spotting, retinal dysplasia (i.e., presence of waves, whorls, and rosettes), increased number of S-opsin-expressing cone cells, degeneration of photoreceptor cells (i.e., rods and cones), and decreased rod cell, long cone cell, and M-cone-cell function in the subject. These clinical, morphological, and functional defects can be measured using standard methods in the art and as described herein. Retinal dysplasia, for example, can be identified or determined using histology and immunostaining. Retinal spotting can be identified or quantified by fundus photography. Retinal integrity, visual acuity/function, and retinal degeneration can be determined by electroretinogram analysis.

Electroretinography measures the electrical responses of various cell types in the retina, including the photoreceptors (rods and cones), inner retinal cells (bipolar and amacrine cells) and the ganglion cells. Electrodes are usually placed on the cornea and the skin near the eye to record the ERG. During a recording, the patient's eyes are exposed to standardized stimuli and the resulting signal is displayed showing the time course of the signal's amplitude (voltage). Signals are very small, and typically are measured in microvolts or nanovolts. The ERG is composed of electrical potentials contributed by different cell types within the retina, and the stimulus conditions (flash or pattern stimulus, whether a background light is present, and the colors of the stimulus and background) can elicit stronger response from certain components. Clinically used mainly by ophthalmologists, the electroretinogram (ERG) is used for the diagnosis of various retinal diseases.

Photopic and scotopic responses are measured under different stimuli conditions to differentiate between visual signal and response from rod and cones. Under photopic conditions (i.e., luminance greater than 3 $cd/m^2$), the rods are saturated and only the cones are producing visual signal.

Under scotopic conditions (i.e., luminance less than 0.03 cd/m$^2$), the light levels are too low to activate the cones, but the rods respond. Other components of the visual response can be identified and compared to determine restoration of photoreceptor or visual function, such as the a-wave, b-wave, c-wave, d-wave and m-wave.

As used herein, "normalize" a level or activity refers to bringing the level or activity of a photoreceptor or photopigment to within the normal range, i.e., the level or activity range as determined from a subject not suffering from the ocular disease or disorder. For example, the methods and composition described herein induce normalization of visual response as measured by electroretinogram, such that the amplitude in response to scotopic condition is at least greater than 100 microvolts; and the amplitude in response to photopic condition is at least greater than 50 microvolts.

As used herein, an "increase" in a level or activity of a nuclear hormone receptor, a downstream signaling component (i.e., phototransducin), or a photoreceptor can be measured by methods known in the art, such as RT-PCR, Western blot, transactivation assays, or electroretinography. An increase in expression level or activity can be 1%, 2%, 5%, 10%, 25%, 50%, 75%, 1-fold, 2-fold, 5-fold, or 10-fold reduced when compared to expression level or activity before treatment, or to expression level or activity in subjects that are suffering from the ocular disease or disorder that have not received treatment. Similarly and as described herein, a "decrease" in a level or activity of a nuclear hormone receptor, a downstream signaling component (i.e., phototransducin), or a photoreceptor can be measured by methods known in the art, such as RT-PCR, Western blot, transactivation assays, or electroretinography, can be measured by methods known in the art, such as RT-PCR or transactivation assays. A reduction in expression level or activity can be 1%, 2%, 5%, 10%, 25%, 50%, 75%, 1-fold, 2-fold, 5-fold, or 10-fold reduced when compared to expression level or activity before treatment, or to expression level or activity in subjects that are suffering from the ocular disease or disorder that have not received treatment.

The mammal can be any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Preferably, composition of the present invention reduces the expression or activity of a cone photoreceptor specific transducin, wherein the cone photoreceptor specific transducin comprises Gnat2. Alternatively or in addition, the composition of the present invention reduces the expression or activity of an S-cone-specific opsin, wherein the S-cone specific opsin comprises Opn1sw.

A suitable nucleic acid sequence of human Nr1d1 is set forth in SEQ ID NO: 5 or a fragment thereof. Alternatively, a suitable nucleic acid sequence encodes human Nr1d1 comprising the amino acid sequence SEQ ID NO: 6, or a fragment thereof. A suitable nucleic acid sequence of human Nr2e3 is set forth in SEQ ID NO: 7 or a fragment thereof. Alternatively, a suitable nucleic acid sequence encodes human Nr2e3 comprising the amino acid sequence SEQ ID NO: 8, or a fragment thereof. A suitable nucleic acid sequence of human Rora is set forth in SEQ ID NO: 9 or a fragment thereof. Alternatively, a suitable nucleic acid sequence encodes human Rora comprising the amino acid sequence SEQ ID NO: 10, or a fragment thereof. A suitable nucleic acid sequence of human Nupr1 is set forth in SEQ ID NO: 28 or a fragment thereof. Alternatively, a suitable nucleic acid sequence encodes human Nupr1 comprising the amino acid sequence SEQ ID NO: 29, or a fragment thereof. A suitable nucleic acid sequence of human Nr2c1 is set forth in SEQ ID NO: 11 or a fragment thereof. Alternatively, a suitable nucleic acid sequence encodes human Nr2c1 comprising the amino acid sequence SEQ ID NO: 12, or a fragment thereof.

Administration is local to the ocular or adnexal tissues. Preferably, the composition is administered intravitreally, sub-retinally, or topically. Topical ophthalmic formulations include eye drops. Preferably, the methods do not include systemic administration. Local ocular administration has several advantages as the eye is an immune-privileged environment and compounds administered to the eye function locally and have little or no systemic dissemination.

The composition is administered at a concentration of 0.001 μg to 100 μg, e.g., 0.01 μg, 0.1 μg, 0.5 μg, 1.0 μg, 1.5 μg, 2.0 μg, 5.0 μg, 10 μg, 20 μg, 30 μg, 40 μg, 50 μg, 60 μg, 70 μg, 80 μg, 90 μg, or 100 μg. The composition is administered in a volume of 0.01 μl to 10 μl, e.g., 0.1 μl, 0.25 μl, 0.5 μl, 1 μl, 1.5 μl, 2 μl, 2.5 μl, 3 μl, 3.5 μl, 4 μl, 4.5 μl, 5 μl, 6 μl, 7 μl, 8 μl, 9 μl, or 10 μl. The composition is administered once per day, once per week, once per month, every 3 months, every 6 months, or every 12 months. The composition is administered for the duration of 1 day, 1 week, 1 month, 3 months, 6 months, 1 year, 2 years, or 5 years.

The composition comprising a nucleic acid, i.e., a nucleic acid vector, is administered via electroporation. Alternatively, the composition is administered via biodegradable Nile red poly(lactide-co-glycolide) (PLGA) nanoparticle-based gene delivery, small molecule-based gene delivery, naked DNA delivery, viral-based gene delivery, e.g., adeno-associated virus delivery, or genome editing systems, e.g., CRISPR.

Optionally, the method further comprises the administration of a pharmaceutically acceptable carrier. The phrase "pharmaceutically acceptable" is art-recognized and refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Optionally, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The polynucleotides, polypeptides (e.g., large proteins), peptides (e.g., small or medium-sized proteins), antibodies, or other biological agents are purified and/or isolated.

Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques.

Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) Proteins, W.H. Freeman and Company, incorporated herein by reference.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide.

Although the phrase "nucleic acid molecule" primarily refers to the physical nucleic acid and the phrase "nucleic acid sequence" refers to the linear list of nucleotides of the nucleic acid molecule, the two phrases can be used interchangeably.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to reduce or prevent ocular disease in a mammal. Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, e.g., ocular disease, so as to effect a reduction in severity and/or frequency of symptoms, eliminate the symptoms and/or their underlying cause, and/or facilitate improvement or remediation of damage.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIGS. 1A-1E are a series of photomicrographs and a pie chart showing that rd7 phenotypes are suppressed in N6 B6. Cg-Mor7$^{AKR/J}$:Nr2e3$^{rd7/rd7}$ mice. FIG. 1A and FIG. 1B are photomicrographs showing hematoxylin and eosin staining of retinal sections from affected (FIG. A) and suppressed (FIG. B) F$_2$ B6. Cg-Mor7$^{AKR/J}$:Nr2e3$^{rd7/rd7}$ P30 animals. Retinal dysplasia was absent in the suppressed rd7 homozygote animals. FIG. 1C and FIG. 1D are photomicrographs showing labeling of retinal sections with OPN1SW-specific antibody. The blue cone population is restored to a normal level in (FIG. C) affected and (FIG. D) suppressed F2 B6. Cg-Mor7$^{AKR/J}$:Nr2e3$^{rd7/rd7}$ animals. FIG. 1E is a pie chart showing the distribution of the 95 retinal genes that map to the Mor7 interval. GCL: ganglion cell layer, INL: inner nuclear layer, ONL: outer nuclear layer, OS: outer segments, RPE: retinal pigment epithelium.

FIG. 2A shows C57BL/6J and AKR/J chromatograms of polymorphisms identified in the ligand-binding domain of Nr1d1, resulting in arginine to glutamine substitution in AKR/J at position 408. FIG. 2B is a ClustalW2 sequence alignment of amino acid sequences from C57BL/6J, AKR/J, rat, chimpanzee and human. Stars indicate identity in all sequences, while dots indicate conserved amino acids. FIG. 2C are C57BL/6J and AKR/J chromatograms of polymorphisms identified in the Nr1d1 5'UTR region. FIG. 2D is a ClustalW2 sequence alignment across species that reveals the consensus is in accordance with AKR/J sequence. Stars indicate nucleotide conservation in all species. FIG. 2E is a bar chart showing Nr1d1 relative expression in P30.5 AKR/J and C57BL/6J retinas (n=3, p=0.0024).

FIGS. 3A-3L is a series of photomicrographs and line graphs showing gene delivery of Nr2e3 or Nr1d1 suppresses pan-retinal spotting, retinal dysplasia and function in Nr2e3$^{rcr/rd7}$ mice. FIGS. 3A-3F show fundus photographs of control and rd7 injected retinas: (FIG. 3A) B6 (uninjected), (FIG. 3B) rd7 (uninjected), (FIG. 3C) GFP injected, (FIG. 3D) GFP.Nr2e3$^{B6}$ injected, (FIG. 3E) GFP.Nr1d1$^{AKR/J}$ injected, (FIG. 3F) GFP.Nr1d1$^{B6}$ injected. FIGS. 3G-3J show DAPI staining (blue) show rescue of defects in retinal morphology 30 days after electroporation into rd7 neonatal retinas with (FIG. 3G) GFP control, (FIG. 3H) Nr2e3$^{B6}$ injected, (FIG. 3I) GFP control, (FIG. 3J) Nr1d1$^{AKR/J}$ injected. L: left, R: right, GCL: ganglion cell layer, INL: inner nuclear layer, ONL: outer nuclear layer. Scale bar=50 FIG. 3K and FIG. 3L show representative (k) scotopic and (l) photopic electroretinograms from animals 4 month after injection with GFP (blue) or GFP.Nr1d1$^{AKR/J}$ (red).

(FIG. 6A) GFP expression in the outer nuclear layer (ONL) and inner nuclear layer (INL) of the retina. (FIG. 6B) GFP expression colocalizes with nuclear marker DAPI. ONL: outer nuclear layer; INL: inner nuclear layer; and RPE: retinal pigment epithelium.

FIG. 7B) rd7 mice exhibit white spots over the entire retina (right panel) and retinal waves (left panel) in comparison to FIG. 7A) control mice.

DETAILED DESCRIPTION OF THE INVENTION

Figure 1E:
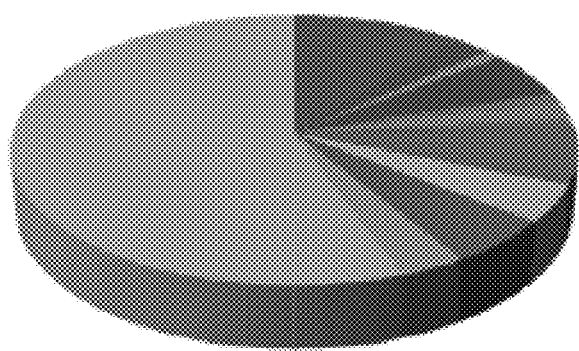

The identification of genetic basis for disease has led to a greater understanding of many ocular diseases. Primary mutations in more than 300 genes have been associated with vision loss, and phenotypic variation is often observed for several ocular diseases caused by known primary mutations. Thus, genetic background greatly affects the phenotypic outcome of a disease and polymorphisms in other genes, modifier genes, affect severity, age of onset, and disease progression.

Described in detail below is the identification of genetic modifiers of ocular disease, i.e., genes that rescue disease caused by a mutation in another gene. The nuclear hormone receptor, Nr2e3, is a retinal-specific transcription factor with critical functions in photoreceptor cell development and differentiation. Mutations in Nr2e3 have been associated with several eye disorders characterized by progressive retinal degeneration, such as enhanced s-cone syndrome (ESCS) and retinitis pigmentosa. Prior to the invention described herein, there were no effective treatment options for this group of diseases.

The retinal degeneration 7 (rd7) mouse model, which lacks Nr2e3 expression, has been a valuable tool for identifying genetic modifiers of Nr2e3-associated hereditary retinal degeneration. As described in detail below, the genetic background of the Nr2e3 mutation highly influences the disease phenotype. For example, B6.Cg-Nr2e3$^{rd7/rd7}$ mice undergo degeneration, while inbreed mouse strains CAST/EiJ, AKR/J and NOD.NON-H2$^{nb1}$ confer resistance to Nr2e3-associated degeneration (Haider et al., 2008 Mamm Genome, 19: 145-154). One of the modifier alleles was identified as the nuclear receptor gene Nr1d1 (also known as Rev-erb alpha). This discovery led to the identification of nucleic acids containing genes that modulate the biological pathways for normal development and normal function of photoreceptor cells in the retina. For example, these nucleic acids contain genes that restore the function of photoreceptor cells and/or prevent the onset or progression of retinal degeneration associated with various ocular diseases.

Nuclear Hormone Receptors

Nuclear receptors represent an evolutionarily conserved group of transcription factors that regulate genes involved in diverse functions such as homeostasis, reproduction, development, metabolism and immune response. Nuclear receptors bind to lipophilic-ligands such as steroid hormones, thyroid hormone, vitamin D and retinoids, which modulate transcriptional activity. Nuclear receptors also function with co-activators or co-repressors to activate or repress the transcription of genes involved in the development and maintenance of specific cell types. In the retina, nuclear hormone receptors regulate the development and patterning of many cell types, such as photoreceptor cells (i.e., rods and cones).

The present invention provides nucleic acids comprising genes or encoding proteins that modulate the biological pathways associated with photoreceptor development and function. Preferably, the nucleic acids comprise nuclear hormone receptors. The nucleic acid and amino acid sequences of exemplary nuclear hormone receptors, such as Nr1d1, Nr2e3, Rora, Nupr1, and Nr2c1 are listed below.

Nr1d1, also known as Rev-erb alpha and nuclear receptor family 1 group D member 1, is a nuclear hormone receptor that has a diverse role in regulating gene networks in several biological processes and in many tissue types. Nr1d1 is expressed in retinal progenitor cells during development, and in ganglion cells and photoreceptors of adult retinas.

Human Nr1d1 mRNA (Genbank Accession No. HQ692861.1 (GI:325495532), incorporated herein by reference) is provided below (SEQ ID NO: 5):

```
   1 atgacgaccc tggactccaa caacaacaca ggtggcgtca
     tcacctacat tggctccagt
  61 ggctcctccc caagccgcac cagccctgaa tccctctata
     gtgacaactc caatggcagc
 121 ttccagtccc tgacccaagg ctgtcccacc tacttcccac
     catccccac tggctccctc
 181 acccaagacc cggctcgctc ctttgggagc attccaccca
     gcctgagtga tgacggctcc
 241 ccttcttcct catcttcctc gtcgtcatcc tcctcctcct
     tctataatgg gagcccccct
 301 gggagtctac aagtggccat ggaggacagc agccgagtgt
     cccccagcaa gagcaccagc
 361 aacatcacca agctgaatgg catggtgtta ctgtgtaaag
     tgtgtgggga cgttgcctcg
 421 ggcttccact acggtgtgca cgcctgcgag ggctgcaagg
     gcttttccg tcggagcatc
 481 cagcagaaca tccagtacaa aaggtgtctg aagaatgaga
     attgctccat cgtccgcatc
 541 aatcgcaacc gctgccagca atgtcgcttc aagaagtgtc
     tctctgtggg catgtctcga
 601 gacgctgtgc gttttgggcg catccccaaa cgagagaagc
     agcggatgct tgctgagatg
 661 cagagtgcca tgaacctggc caacaaccag ttgagcagcc
     agtgcccgct ggagacttca
 721 cccacccagc accccacccc aggccccatg ggccctcgc
     cacccctgc tccggtcccc
 781 tcaccctgg tgggcttctc ccagtttcca caacagctga
     cgcctcccag atcccaagc
 841 cctgagccca cagtggagga tgtgatatcc caggtggccc
     gggcccatcg agagatcttc
 901 acctacgccc atgacaagct gggcagctca cctggcaact
     tcaatgccaa ccatgcatca
 961 ggtagccctc cagccaccac cccacatcgc tgggaaaatc
     agggctgccc acctgccccc
1021 aatgacaaca cacccttggc tgcccagcgt cataacgagg
     ccctaaatgg tctgcgccag
1081 gctccctcct cctaccctcc cacctggcct cctggccctg
     cacaccacag ctgccaccag
1141 tccaacagca acgggcaccg tctatgcccc acccacgtgt
     atgcagcccc agaaggcaag
1201 gcacctgcca acagtcccg gcagggcaac tcaaagaatg
     ttctgctggc atgtcctatg
1261 aacatgtacc cgcatggacg cagtgggcga acggtgcagg
     agatctggga ggattctcc
1321 atgagcttca cgcccgctgt gcgggaggtg gtagagtttg
     ccaaacacat cccgggcttc
1381 cgtgaccttt ctcagcatga ccaagtcacc ctgcttaagg
     ctggcacctt tgaggtgctg
1441 atggtgcgct ttgcttcgtt gttcaacgtg aaggaccaga
     cagtgatgtt cctaagccgc
```

```
-continued
1501 accacctaca gcctgcagga gcttggtgcc atgggcatgg
     gagacctgct cagtgccatg
1561 ttcgacttca gcgagaagct caactccctg gcgcttaccg
     aggaggagct gggcctcttc
1621 accgcggtgg tgcttgtctc tgcagaccgc tcgggcatgg
     agaattccgc ttcggtggag
1681 cagctccagg agacgctgct gcgggctctt cgggctctgg
     tgctgaagaa ccggcccttg
1741 gagacttccc gcttcaccaa gctgctgctc aagctgccgg
     acctgcggac cctgaacaac
1801 atgcattccg agaagctgct gtccttccgg gtggacgccc
     agtga
```

The amino acid sequence for human Nr1d1 is provided below (SEQ ID NO: 6). Similar to other nuclear hormone receptors, Nr1d1 has a DNA-binding domain, a hinge region, and a ligand-binding domain. Specifically, the DNA-binding domain is located at amino acid positions 127-215; the hinge region is located at amino acid positions 206-284; and the ligand binding domain is located at amino acid positions 285-614, preferably at amino acids 418-611.

```
  1 mttldsnnnt ggvityigss gsspsrtspe slysdnsngs
    fqsltqgcpt yfppsptgsl
 61 tqdparsfgs ippslsddgs pssssssss sssfyngspp
    gslqvameds srvspsksts
121 nitklngmvl lckvcgdvas gfhygvhace gckgffrrsi
    qqniqykrcl knencsivri
181 nrnrcqqcrf kkclsvgmsr davrfgripk rekqrmlaem
    qsamnlannq lssqcplets
241 ptqhptpgpm gpspppapvp splvgfsqfp qqltpprsps
    peptvedvis qvarahreif
301 tyahdklgss pgnfnanhas gsppattphr wenqgcppap
    ndnntlaaqr hnealnglrq
361 apssypptwp pgpahhschq snsnghrlcp thvyaapegk
    apansprqgn sknvllacpm
421 nmyphgrsgr tvqeiwedfs msftpavrev vefakhipgf
    rdlsqhdqvt llkagtfevl
481 mvrfaslfnv kdqtvmflsr ttyslqelga mgmgdllsam
    fdfseklnsl alteeelglf
541 tavvlvsadr sgmensasve qlqetllral ralvlknrpl
    etsrftklll klpdlrtlnn
601 mhsekllsfr vdaq
```

Nr2e3 is also known as Nuclear Receptor Subfamily 2 Group E Member 3, photoceptor-specific nuclear receptor (PNR); rd7, retina-specific nuclear receptor, and ESPS. Nr2e3 is a nuclear receptor critical for development and maintenance of rod and cone photoreceptor cells. Loss of Nr2e3 causes retinal diseases primarily characterized by photoreceptor degeneration. Mutations of Nr2e3 have been associated with several retinal diseases. Nr2e3 functions as a dual activator and suppressor of gene expression, and together with transcription factors CRX and Nr1d1 modulates photoreceptor cell fate and differentiation. Nr2e3 is also expressed in mature photoreceptors where it regulates expression of genes essential for proper function, for example, phototransducin genes.

Human Nr2e3 mRNA sequence is provided below (SEQ ID NO: 7):

```
  1 ctcagcagca gagttaagta gtattgcttt aattgcaaca
    agctgagcta atgtgggaag
 61 aatgcagtag agtggcacag aagaatgcta acccgaaact
    ctaagcctgt tccctggaat
121 cttccatctg gatggaggag agaaagttga cctggagtga
    ggttcaatgt aaggacaaga
181 tctgcacccg gagaagctct ctctcggaga gcacaggcgg
    cctgaggagt caaaacaggt
241 ggcctgtgga gtcagcacag gcagcctgga ggaggtgagg
    aactgaagtt tggacagatt
301 gagtcacttt ctcagggaca catggctggc cggtgatgga
    gaaggcgtga gcccctcgct
361 ccagtgccgc gtgtgcggag acagcagcag cgggaagcac
    tatggcatct atgcctgcaa
421 cggctgcagc ggcttcttca agaggagcgt acggcggagg
    ctcatctaca ggtgccaggt
481 gggggcaggg atgtgcccg tggacaaggc ccaccgcaac
    cagtgccagg cctgccggct
541 gaagaagtgc ctgcaggcgg ggatgaacca ggacgccgtg
    cagaacgagc gccagccgcg
601 aagcacagcc caggtccacc tggacagcat ggagtccaac
    actgagtccc ggccggagtc
661 cctggtggct ccccggccc cggcagggcg cagcccacgg
    ggccccacac ccatgtctgc
721 agccagagcc ctgggccacc acttcatggc cagccttata
    acagctgaaa cctgtgctaa
781 gctggagcca gaggatgctg atgagaatat tgatgtcacc
    agcaatgacc ctgagttccc
841 ctcctctcca tactcctctt cctcccctg cggcctggac
    agcatccatg agacctcggc
901 tcgcctactc ttcatggccg tcaagtgggc caagaacctg
    cctgtgttct ccagcctgcc
```

```
 961  cttccgggat caggtgatcc tgctggaaga ggcgtggagt
      gaactctttc tcctcgggc
1021  catccagtgg tctctgcctc tggacagctg tcctctgctg
      gcaccgcccg aggcctctgc
1081  tgccggtggt gcccagggcc ggctcacgct ggccagcatg
      gagacgcgtg tcctgcagga
1141  aactatctct cggttccggg cattggcggt ggaccccacg
      gagtttgcct gcatgaaggc
1201  cttggtcctc ttcaagccag agacgcgggg cctgaaggat
      cctgagcacg tagaggcctt
1261  gcaggaccag tcccaagtga tgctgagcca gcacagcaag
      gcccaccacc ccagccagcc
1321  cgtgaggttt gggaaattgc tcctgctcct cccgtctttg
      aggtttatca ctgcggaacg
1381  catcgagctc ctcttttttcc gcaagaccat agggaatact
      ccaatggaga agctcctttg
1441  tgatatgttc aaaaactagt gggggtggag gtgaaatgtt
      tccaagcact ctggaaaaca
1501  atctactgaa acgaaacatt tgcctactct ttgccccagc
      aattcctcgt aggtgtgtgt
1561  acccagcaga aatgcccacc gaaagatatt gtaagaatat
      tcatagcagc tttattcata
1621  atagccccaa actgtatatt gatggtagga tgaattaaca
      agttgtggta tattcatata
1681  atgaaaaata atttaaaaag aatgaattac ggatacatgt
      ggcaacacag gtaaacttca
1741  cagacataaa agttgaatga aagaagccag gccgaagttc
      catttatgca gagttcagga
1801  acaggcaaga ctaattgaca ataatagaag ttggaatagt
      ggttacttct gggtggtggg
1861  ggattgatac agaggggggct catgggagcc ctctggtgta
      ccagaaatgt tgattttgat
1921  ctgggcagtg gtttcacaaa tgtattcata cgtaataatt
      cattgagctg tgcactttat
1981  tttgttagac ctcaataaaa aagtaaaaaa aaaaaaaaa
```

The amino acid sequence for human Nr2e3 is provided below (SEQ ID NO: 8). With regard to Nr2e3, the DNA-binding domain is located at amino acid positions 1-42; the hinge region is located at, for example, amino acid positions 43-103; and the ligand binding domain is located at amino acid positions 104-309.

```
  1  mcpvdkahrn qcqacrlkkc lqagmnqdav qnerqprsta
     qvhldsmesn tesrpeslva
 61  ppapagrspr gptpmsaara lghhfmasli taetcaklep
     edadenidvt sndpefpssp
121  yssssspcgld sihetsarll fmavkwaknl pvfsslpfrd
     qvilleeaws elfllgaiqw
181  slpldscpll appeasaagg aqgrltlasm etrvlqetis
     rfralavdpt efacmkalvl
241  fkpetrglkd pehvealqdq sqvmlsqhsk ahhpsqpvrf
     gklllllpsl rfitaeriel
301  lffrktignt pmekllcdmf kn
```

Rora is also known as RAR-related Orphan Receptor A, ROR-alpha, retinoic acid receptor-related orphan receptor alpha, and Nuclear Receptor Subfamily 1 Group F Member 1 (Nr1f1). Rora is also a member of the NR1 subfamily of nuclear hormone receptors. Rora regulates a number of genes involved in lipid metabolism and photoreceptor development, including PCP2, OPN1SW, OPN1SM, and ARR3. There are four transcripts variants encoding different isoforms. The present invention encompasses all four transcript variants.

Human Rora mRNA sequence is provided below (SEQ ID NO: 9):

```
  1  ccatctgtct gatcaccttg gactccatag tacactgggg
     caaagcacag ccccagtttc
 61  tggaggcaga tgggtaacca ggaaaaggca tgaatgaggg
     ggccccagga gacagtgact
121  tagagactga ggcaagagtg ccgtggtcaa tcatgggtca
     ttgtcttcga actggacagg
181  ccagaatgtc tgccacaccc acacctgcag gtgaaggagc
     cagaagggat gaacttttg
241  ggattctcca aatactccat cagtgtatcc tgtcttcagg
     tgatgctttt gttcttactg
301  gcgtctgttg ttcctggagg cagaatggca agccaccata
     ttcacaaaag gaagataagg
361  aagtacaaac tggatacatg aatgctcaaa ttgaaattat
     tccatgcaag atctgtggag
421  acaaatcatc aggaatccat tatggtgtca ttacatgtga
     aggctgcaag ggcttttttca
481  ggagaagtca gcaaagcaat gccacctact cctgtcctcg
     tcagaagaac tgtttgattg
541  atcgaaccag tagaaaccgc tgccaacact gtcgattaca
     gaaatgcctt gccgtaggga
```

-continued

```
 601 tgtctcgaga tgctgtaaaa tttggccgaa tgtcaaaaaa
     gcagagagac agcttgtatg
 661 cagaagtaca gaaacaccgg atgcagcagc agcagcgcga
     ccaccagcag cagcctggag
 721 aggctgagcc gctgacgccc acctacaaca tctcggccaa
     cgggctgacg gaacttcacg
 781 acgacctcag taactacatt gacgggcaca ccctgaggg
     gagtaaggca gactccgccg
 841 tcagcagctt ctacctggac atacagcctt ccccagacca
     gtcaggtctt gatatcaatg
 901 gaatcaaacc agaaccaata tgtgactaca ccagcatc
     aggcttcttt ccctactgtt
 961 cgttcaccaa cggcgagact tccccaactg tgtccatggc
     agaattagaa caccttgcac
1021 agaatatatc taaatcgcat ctggaaacct gccaatactt
     gagagaagag ctccagcaga
1081 taacgtggca gacctttta caggaagaaa ttgagaacta
     tcaaaacaag cagcgggagg
1141 tgatgtggca attgtgtgcc atcaaaatta cagaagctat
     acagtatgtg gtggagtttg
1201 ccaaacgcat tgatggattt atggaactgt gtcaaaatga
     tcaaattgtg cttctaaaag
1261 caggttctct agaggtggtg tttatcagaa tgtgccgtgc
     ctttgactct cagaacaaca
1321 ccgtgtactt tgatgggaag tatgccagcc ccgacgtctt
     caaatcctta ggttgtgaag
1381 actttattag ctttgtgttt gaatttggaa agagtttatg
     ttctatgcac ctgactgaag
1441 atgaaattgc attattttct gcatttgtac tgatgtcagc
     agatcgctca tggctgcaag
1501 aaaaggtaaa aattgaaaaa ctgcaacaga aaattcagct
     agctcttcaa cacgtcctac
1561 agaagaatca ccgagaagat ggaatactaa caaagttaat
     atgcaaggtg tctacattaa
1621 gagccttatg tggacgacat acagaaaagc taatggcatt
     taaagcaata tacccagaca
1681 ttgtgcgact tcattttcct ccattataca aggagttgtt
     cacttcagaa tttgagccag
1741 caatgcaaat tgatgggtaa atgttatcac ctaagcactt
     ctagaatgtc tgaagtacaa
1801 acatgaaaaa caaacaaaaa aattaaccga gacactttat
     atggccctgc acagacctgg
1861 agcgccacac actgcacatc ttttggtgat cggggtcagg
     caaaggaggg gaaacaatga
1921 aaacaaataa agttgaactt gttttctca
```

The amino acid sequence for human Rora is provided below (SEQ ID NO: 10). The DNA binding domain is located at amino acid positions 99-193; the hinge region is located at amino acid positions 172-304; and the ligand-binding domain is located at amino acid positions 305-544.

```
  1 mnegapgdsd letearvpws imghclrtgq armsatptpa
    gegarrdelf gilqilhqci
 61 lssgdafvlt gvccswrqng kppysqkedk evqtgymnaq
    ieiipckicg dkssgihygv
121 itcegckgff rrsqqsnaty scprqkncli drtsrnrcqh
    crlqkclavg msrdavkfgr
181 mskkqrdsly aevqkhrmqq qqrdhqqqpg eaepltptyn
    isangltelh ddlsnyidgh
241 tpegskadsa vssfyldiqp spdqsgldin gikpepicdy
    tpasgffpyc sftngetspt
301 vsmaelehla qniskshlet cqylreelqq itwqtflqee
    ienyqnkqre vmwqlcaiki
361 teaiqyvvef akridgfmel cqndqivllk agslevvfir
    mcrafdsqnn tvyfdgkyas
421 pdvfkslgce dfisfvfefg kslcsmhlte deialfsafv
    lmsadrswlq ekvkieklqq
481 kiqlalqhvl qknhredgil tklickvstl ralcgrhtek
    lmafkaiypd ivrlhfpply
541 kelftsefep amqidg
```

Nr2c1 is also known as Nuclear Receptor Subfamily 2 Group C Member 1, TR2, and orphan nuclear receptor TR2.

Human Nr2c1 mRNA sequence is provided below (SEQ ID NO: 11):

```
  1 gcttctcccc gttgctaatg cgcaggcgct ggcgggatag
    cgcgccgccg agccgagaaa
 61 gaggtcacga actctgaccc cccagaaata cccaaacaca
    gaaagctctc tccgccgtga
121 atctcgatcc cacatcccgt cggctttctt caacctctct
    tcccggagcg ccccccaatc
181 cacgagtggc agccgcggga ctgtcgcgtc ggcgcccgac
    gccggagtca gcagggcgca
```

-continued

```
 241 aaagcgccgg tagatcatgg caaccataga agaaattgca
     catcaaatta ttgaacaaca
 301 gatgggagag attgttacag agcagcaaac tgggcagaaa
     atccagattg tgacagcact
 361 tgatcataat acccaaggca agcagttcat tctgacaaat
     cacgacggct ctactccaag
 421 caaagtcatt ctggccaggc aagattccac tccgggaaaa
     gttttcctta caactccaga
 481 tgcagcaggt gtcaaccagt tattttttac cactcctgat
     ctgtctgcac aacacctgca
 541 gctcctaaca gataattctc cagaccaagg accaaataag
     gtttttgatc tttgcgtagt
 601 atgtggagac aaagcatcag gacgtcatta tggagcagta
     acttgtgaag ctgcaaagg
 661 atttttttaaa agaagcatcc gaaaaaattt agtatattca
     tgtcgaggat caaaggattg
 721 tattattaat aagcaccacc gaaaccgctg tcaatactgc
     aggttacaga gatgtattgc
 781 gtttggaatg aagcaagact ctgtccaatg tgaaagaaaa
     cccattgaag tatcacgaga
 841 aaaatcttcc aactgtgccg cttcaacaga aaaaatctat
     atccgaaagg accttcgtag
 901 cccattaact gcaactccaa cttttgtaac agatagtgaa
     agtacaaggt caacaggact
 961 gttagattca ggaatgttca tgaatattca tccatctgga
     gtaaaaactg agtcagctgt
1021 gctgatgaca tcagataagg ctgaatcatg tcagggagat
     ttaagtacat tggccaatgt
1081 ggttacatca ttagcgaatc ttggaaaaac taaagatctt
     tctcaaaata gtaatgaaat
1141 gtctatgatt gaaagcttaa gcaatgatga tacctctttg
     tgtgaatttc aagaaatgca
1201 gaccaacggt gatgtttcaa gggcatttga cactcttgca
     aaagcattga atcctggaga
1261 gagcacagcc tgccagagct cagtagcggg catggaagga
     agtgtacacc taatcactgg
1321 agattcaagc ataaattaca ccgaaaaaga ggggccactt
     ctcagcgatt cacatgtagc
1381 tttcaggctc accatgcctt ctcctatgcc tgagtacctg
     aatgtgcact acattgggga
```

```
1441 gtctgcctcc agactgctgt tcttatcaat gcactgggca
     ctttcgattc cttctttcca
1501 ggctctaggg caagaaaaca gcatatcact ggtgaaagct
     tactggaatg aactttttac
1561 tcttggtctt gcccagtgct ggcaagtgat gaatgtagca
     actatattag caacatttgt
1621 caattgtctt cacaatagtc ttcaacaaga tgccaaggta
     attgcagccc tcattcattt
1681 cacaagacga gcaatcactg atttataaat gcttaactat
     agaatggctt atgactaccc
1741 aaaacagtgc cccatcaaca aatggggaaa attgcctttt
     gagctcagga ataatttata
1801 aattggggac tacctttttag ttctttagca tattctattt
     cttattgttt tatataattt
1861 ttaaatcatt tgcttcctcc ttatgtttaa cagcagaggg
     gtaatcacct taaaatgtca
1921 tcaaaaatag atctactaga aggcagcatc acattcccat
     cttacttatg gactcctacc
1981 cctggttcat gtcttatatg cctgtaatgg ttataaagcc
     taccttcagg aaagctatgg
2041 ttgactaatt actaatggat gggttttaaa catgtccctc
     tacaataaat taaaatcttt
2101 attgtaaaac tttaaaaaaa aaaaaaaaaa aaaaaaaaa
     aaaaaaa
```

The amino acid sequence for human Nr2c1 is provided below (SEQ ID NO: 12). The DNA binding domain is located at amino acid positions 108-194; the hinge region is located at amino acid positions, for example, 195-367; and the ligand-binding domain is located at amino acid positions 368-589.

```
  1 MATIEEIAHQ IIEQQMGEIV TEQQTGQKIQ IVTALDHNTQ
    GKQFILTNHD GSTPSKVILA
 61 RQDSTPGKVF LTTPDAAGVN QLFFTTPDLS AQHLQLLTDN
    SPDQGPNKVF DLCVVCGDKA
121 SGRHYGAVTC EGCKGFFKRS IRKNLVYSCR GSKDCIINKH
    HRNRCQYCRL QRCIAFGMKQ
181 DSVQCERKPI EVSREKSSNC AASTEKIYIR KDLRSPLTAT
    PTFVTDSEST RSTGLLDSGM
241 FMNIHPSGVK TESAVLMTSD KAESCQGDLS TLANVVTSLA
    NLGKTKDLSQ NSNEMSMIES
301 LSNDDTSLCE FQEMQTNGDV SRAFDTLAKA LNPGESTACQ
    SSVAGMEGSV HLITGDSSIN
```

```
361  YTEKEGPLLS  DSHVAFRLTM  PSPMPEYLNV  HYIGESASRL

LFLSMHWALS  IPSFQALGQE

421  NSISLVKAYW  NELFTLGLAQ  CWQVMNVATI  LATFVNCLHN

SLQQDKMSTE  RRKLLMEHIF

481  KLQEFCNSMV  KLCIDGYEYA  YLKAIVLFSP  DHPSLENMEL

IEKFQEKAYV  EFQDYITKTY

541  PDDTYRLSRL  LLRLPALRLM  NATITEELFF  KGLIGNIRID

SVIPHILKME  PADYNSQIIG

601  HSI
```

Nupr1 is also known as nuclear protein 1. Human Nupr1 mRNA sequence is provided below (SEQ ID NO: 28):

```
  1  caaagcgtta  ggagaagaag  agaggcaggg  aagacaagcc aggcacgatg  gccaccttcc 61  caccagcaac  cagcgccccc  cagcagcccc  caggcccgga ggacgaggac  tccagcctgg 121  atgaatctga  cctctatagc  ctggcccatt  cctacctcgg aggtggaggc  cggaaaggtc 181  gcaccaagag  agaagctgct  gccaacacca  accgccccag ccctggcggg  cacgagagga 241  aactggtgac  caagctgcag  aattcagaga  ggaagaagcg aggggcacgg  cgctgagaca 301  gagctggaga  tgaggccaga  ccatggacac  tacacccagc aatagagacg  ggactgcgga 361  ggaaggagga  cccaggacag  gatccaggcc  ggcttgccac accccccacc  cctaggactt 421  attcccgctg  actgagtctc  tgaggggcta  ccaggaaagc gcctccaacc  ctagcaaaag 481  tgcaagatgg  ggagtgagag  gctgggaatg  gaggggcaga gccaggaaga  tcccccagaa 541  aagaaagcta  cagaagaaac  tggggctcct  ccagggtggc agcaacaata  aatagacacg 601  cacggcagcc  acaaaaaaaa  aaaaaaaaaa  aaaaaaaaaa aaaaaaaaaa  aaaaaaaa
```

The amino acid sequence for human Nupr1 is provided below (SEQ ID NO: 29):

```
  1  matfppatsa  pqqppgpede  dssldesdly  slahsylggg grkgrtkrea  aantnrpspg 61  gherklytkl  qnserkkrga  rr
```

The present invention is also directed to nucleic acids that encode a biologically active fragment or a variant of Nr1d1, Nr2e3, Rora, Nupr1, or Nr2c1. A biologically active fragment or variant is a "functional equivalent"—a term that is well understood in the art and is further defined in detail herein. The requisite biological activity of the fragment or variant, using any method disclosed herein or known in the art to establish activity of a nuclear hormone receptor, has the following activity relative to the wild-type native polypeptide: about 50%, about 55%, about 60%, about 65%, about 70%, about 75%, about 80%, about 85%, about 90%, about 95%, about 99%, and any range derivable therein, such as, for example, from about 70% to about 80%, and more preferably from about 81% to about 90%; or even more preferably, from about 91% to about 99%.

A fragment, in the case of these sequences and all others provided herein, is defined as a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the nuclear hormone receptors disclosed herein is about 10 amino acids, about 20 amino acids, about 30 amino acids, about 40 amino acids, about 50 amino acids, about 60 amino acids, about 70 amino acids, about 80 amino acids, about 90 amino acids, about 100 amino acids, about 150 amino acids, about 200 amino acids, about 250 amino acids, about 300 amino acids, about 350 amino acids, about 400 amino acids, about 450 amino acids, about 500 amino acids, about 550 amino acids, about 600 amino acids, about 650 amino acids, or about 700 amino acids long. For example, fragments of any of the nuclear hormone receptors disclosed herein is about 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 750 nucleotides, 800 nucleotides, 850 nucleotides, 900 nucleotides, 950 nucleotides, 1000 nucleotides, 1100 nucleotides, 1200 nucleotides, 1300 nucleotides, 1400 nucleotides or 1500 nucleotides long.

In some preferred embodiments, the fragments of the present invention comprise or consist primarily of the specific domains that are required for or contribute to functional activity of Nr1d1, Nr2e3, Rora, Nupr1, or Nr2c1. For example, nuclear hormone receptors comprise evolutionary conserved domains shared with all members of the family, including: the highly variable A/B domain, N terminal DNA binding domain, a flexible hinge region and the ligand-binding and dimerization domain in the C terminus.

Variants encompassed by the present invention include nucleic acid or amino acid sequences comprising the following degrees of sequence identity to Nr1d1, Nr2e3, Rora, Nupr1, or Nr2c1: about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, from about 70% to about 80%, and more preferably from about 81% to about 90%; or even more preferably, from about 91% to about 99% identity.

It should be appreciated that any variations in the coding sequences of the present nucleic acids that, as a result of the degeneracy of the genetic code, express a polypeptide of the same sequence, are included within the scope of this invention.

The term "% identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared.

Nucleic acid and amino acid sequence identity can be determined using standard methods, typically based on certain mathematical algorithms. In a preferred embodiment, the percent identity between two nucleic acid or amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers and Miller (CABIOS, 4:11-17 (1989)) which has been incorporated into the ALIGN program (version 2.0), using a PAM120 weight residue table, a gap length penalty of 12 and a gap penalty of 4. The nucleotide and amino acid sequences of the present invention can further be used as a "query sequence" to perform a search against public databases, for example, to identify other family members or related sequences. Such searches can be performed using the NBLAST and XBLAST programs (Altschul et al. (1990) *J. Mol. Biol.* 215:403-10). BLAST nucleotide searches can be performed with the NBLAST program to obtain nucleotide sequences homologous to nucleic acids of the present invention, e.g., Nr1d1, Nr2e3, Rora, Nupr1, or Nr2c1. BLAST protein searches can be performed with the XBLAST program to obtain amino acid sequences homologous to the appropriate reference protein, e.g., Nr1d1, Nr2e3, Rora, Nupr1, or Nr2c1. To obtain gapped alignments for comparison purposes, Gapped BLAST can be utilized (Altschul et al. (1997) *Nucleic Acids Res.* 25:3389-3402). When utilizing BLAST and Gapped BLAST programs, the default parameters of the respective programs (e.g., XBLAST and NBLAST) can be used.

Any of a number of known recombinant methods are used to produce a DNA molecule encoding the fragment or variant. For production of a variant, it is routine to introduce mutations into the coding sequence to generate desired amino acid sequence variants of the invention. Site-directed mutagenesis is a well-known technique for which protocols and reagents are commercially available (e.g., Zoller, M J et al., 1982, *Nucl Acids Res* 10:6487-6500; Adelman, J P et al., 1983, *DNA* 2:183-93). These mutations include simple deletions or insertions, systematic deletions, insertions or substitutions of clusters of bases or substitutions of single bases.

Methods of Treatment

The present invention is based upon the discovery of a gene therapy approach in which a modifier gene is administered to the ocular or adnexal tissue for the treatment or prevention of disease. By "modifier gene" is meant a gene that affects the phenotypic expression of another gene(s). For example, the modifier genes are administered via electroporation. Alternatively, the modifier gene is administered via biodegradable Nile red poly(lactide-co-glycolide) (PLGA) nanoparticle-based gene delivery, naked DNA delivery, small molecule-based gene delivery, or viral-based gene delivery, e.g., adeno-associated virus delivery. These techniques are utilized alone or in combination to ameliorate or reduce the severity of ocular disease or disorder.

In one embodiment, the invention also features a vector or a nucleic acid construct, e.g., a vector containing the nucleic acids described herein. The vector can further include one or more regulatory elements, e.g., a heterologous promoter.

A variety of known nucleic acid vectors may be used in these methods, e.g., recombinant viruses, such as recombinant adeno-associated virus (rAAV), recombinant adenoviruses, recombinant retroviruses, recombinant poxviruses, and other known viruses in the art, as well as plasmids, cosmids and phages, etc. Many publications well-known in the art discuss the use of a variety of such vectors for delivery of genes. See, e.g., Ausubel et al., *Current Protocols in Molecular Biology*, John Wiley & Sons, New York, latest edition; Kay, M A. et al., 2001, *Nat. Med.*, 7:33-40; and Walther W et al., 2000, *Drugs* 60:249-71). The regulatory elements may be endogenously found upstream or downstream of the genes, or they may be exogenous regulatory elements that are not found to regulate the genes in nature, and introduced by recombinant DNA techniques known in the art. The regulatory elements can be operably linked to a gene or fragment thereof of the present invention, or a gene encoding a protein or fragment thereof of the present invention. Methods for assembly of the recombinant vectors are well-known. See, for example, WO 00/15822 and other references cited therein, all of which are incorporated by reference. Upon delivery of the vector to the subject, i.e., to the eye of the subject, the nucleic acid is optionally integrated into the genome of the cells of the eye, i.e., photoreceptor cells, cells of the outer nuclear layer, cells of the inner nuclear layer, or retinal pigment epithelium.

The vectors of present invention includes appropriate sequences operably linked to the coding sequence or ORF to promote expression of the nuclear hormone receptors of the present invention in a targeted host cell. "Operably linked" sequences include both expression control sequences such as promoters that are contiguous with the coding sequences and expression control sequences that act in trans or distally to control the expression of the polypeptide product.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance nucleic acid or protein stability; and when desired, sequences that enhance protein processing and/or secretion. Many varied expression control sequences, including native and non-native, constitutive, inducible and/or tissue-specific, are known in the art and may be utilized herein, depending upon the type of expression desired.

Expression control sequences for eukaryotic cells typically include a promoter, an enhancer, such as one derived from an immunoglobulin gene, SV40, CMV, etc., and a polyadenylation sequence which may include splice donor and acceptor sites. The polyadenylation sequence generally is inserted 3' to the coding sequence and 5' to the 3' ITR sequence. PolyA from bovine growth hormone is a suitable sequence.

The promoter may be selected from a number of constitutive or inducible promoters that can drive expression of the selected transgene in an ocular setting, preferably in retinal neurons. A preferred promoter is "cell-specific", meaning that it is selected to direct expression of the selected transgene in a particular ocular cell type, such as photoreceptor cells. In some embodiments, an inducible promoter may be preferred.

The rAAV used in the present invention may be constructed and produced using the materials and methods described herein and those well-known in the art. The methods that are preferred for producing any construct of this invention are conventional and include genetic engineering, recombinant engineering, and synthetic techniques readily understood by the ordinarily skilled artisan.

Briefly, to package an rAAV construct into an rAAV virion, a sequences necessary to express AAV rep and AAV cap or functional fragments thereof as well as helper genes essential for AAV production must be present in the host cells. See, for example U.S. Patent Pub. 2007/0015238, which describes production of pseudotyped rAAV virion vectors encoding AAV Rep and Cap proteins of different serotypes and AdV transcription products that provide helper functions. For example, AAV rep and cap sequences may be introduced into the host cell in any known manner including, without limitation, transfection, electroporation, liposome delivery, membrane fusion, biolistic deliver of DNA-coated pellets, viral infection and protoplast fusion. Devices specifically adapted for delivering DNA to specific regions within and around the eye for the purpose of gene therapy have been described recently (for example, U.S. Patent Pub. 2005/0277868, incorporated by reference) are used within the scope of this invention. Such devices utilize electroporation and electromigration, providing, e.g., two electrodes on a flexible support that can be placed behind the retina. A third electrode is part of a hollow support, which can also be used to inject the molecule to the desired area. The electrodes can be positioned around the eye, including behind the retina or within the vitreous.

These sequences may exist stably in the cell as an episome or be stably integrated into the cell's genome. They may also be expressed more transiently in the host cell. The level of RNA expression may be monitored by Northern blots quantitative RT-PCR. The level of protein expression may be monitored by Western blot, immunohistochemistry, immunoassay including enzyme immunoassay (EIA) such as enzyme-linked immunosorbent assays (ELISA), radioimmunoassays (RIA) or by other methods.

In another preferred embodiment, the nucleic acids of the present invention can be delivered via nanoparticles. The nanoparticles are, for example, lipid-based colloidal particles with a diameter of less than 100 nm. Nanoparticles intended for drug and gene delivery can be characterized for various parameters including particle size, size distribution, morphology, zeta potential, drug loading, syringeability and injectability, in vitro drug release, and stability. The formulation of the nanoparticles varies, with respect to lipid composition, nucleic acid to lipid ratio, and formulation method, depending on the intended use. Nanoparticle assembly methods are known in the art, and as described in Kompella et al., "Nanoparticles for Drug and Gene Delivery in Treating Diseases of the Eye"; Methods in Pharmacology and Toxicology, 2014, pages 291-316. In a preferred embodiment, the nanoparticle is a hybrid polyamidoamine (PAMAM) dendrimer hydrogel/poly(lactic-co-glycolic acid) (PLGA) suitable for topical administration.

Genome editing systems can also be used to deliver nucleic acids of the present invention to the eye. Examples of such genome editing systems include, but are not limited to: CRISPR/Cas systems, zinc finger nucleases (ZFNS), and transcription activator-like effector nucleases (TALENS). In such systems, the nucleic acids of the present invention can be readily incorporated into the host cell genome and expressed. In some embodiments, mutated forms of disease-causing genes (i.e., Nr2e3) can be "edited", or selectively excised, and replaced with any of the nucleic acids described herein. Expression is modulated by endogenous or exogenous regulatory elements, and expressed of these nucleic acids improves or ameliorates the symptoms of the disease.

The methods and compositions described herein refer to the restoration or normalization of visual responses. As used herein, the "restoration" or "normalization" refers to increasing or decreasing the expression level or activity of photoreceptors to that of a subject that does not suffer from an ocular disease or disorder, i.e., a subject that does not display photoreceptor degeneration. The restoration or normalization of photoreceptor activity or visual response can be measured or determined by electroretinography. Standards for normal ranges of photoreceptor or visual response as measured by electroretinography have been extensively studied and are established in the art (Perlman, Ido, Chapter XI: The Electroretinogram: ERG by Ido Perlman; Webvision: The Organization of the Retina and Visual System; and Kremers J et al., Prog Retin eye Res. 2003, 22(5):579-605; both references are incorporated herein by reference in their entireties).

As described in detail below, gene delivery of Nr1d1 into the eyes of rd7 mice efficiently ameliorated clinical, morphological, and functional defects associated with rd7 retinal degeneration. Following the administration of the cDNA or nanoparticles, a partial rescue of the rd7 phenotypes was observed both by fundus examinations as well as electroretinogram (ERG) analysis of photoreceptor function. As described herein, in vivo electroporation was utilized to deliver cDNA of modifier genes (such as Nr1d1) into the eyes of rd7 mice. Additionally, biodegradable Nile red poly(lactide-co-glycolide) (PLGA) nanoparticles was utilized as a non-viral alternative delivery method.

Genetic heterogeneity is observed for many Mendelian, single gene disorders (Wolf, U., 1997 Hum Genet, 100: 305-321). While environmental influences may provide minor contributions, variations in phenotypic outcome are generally attributable to allelic heterogeneity or genetic modifier genes. Genetic modifiers are allelic variants, distinct from the mutant gene that can alter disease outcome by either increasing or reducing disease severity, and affect disease onset and progression (Houlston, R. S. & Tomlinson, I. P., 1998 Eur J Hum Genet, 6: 80-88). Identification of genetic modifiers has a significant impact in prediction of disease progression and development of new therapeutic strategies. Mouse models provide a unique platform to uncover genetic modifiers that influence phenotypic variation in human disease (Hamilton, B. A. & Yu, B. D., PLoS Genet, 8: e1002644). For example, mouse models of cystic fibrosis in combination with genome-wide studies in patients have uncovered several pathways that can modify the disease, leading to a better understanding of cystic fibrosis etiology and novel strategies for therapeutic development (Cutting, G. R., 2005 Annu Rev Genomics Hum Genet, 6: 237-260; Cutting, G. R. Ann N Y Acad Sci, 1214:

57-69; Collaco, J. M. & Cutting, G. R., 2008 Curr Opin Pulm Med, 14: 559-566). Significant disease variability is also prevalent for many inherited retinal degenerative diseases; however, the underlying causes for such variations have not been defined for most cases (Zernant et al., 2005 Invest Ophthalmol Vis Sci, 46: 3052-3059; Passerini et al., 2007 Eur J Ophthalmol, 17: 1000-1003; Walia et al., 2008 Arch Ophthalmol, 126: 379-384; Fahim et al., 2011 PLoS One, 6: e23021; Haider et. al., 2002 Hum Mol Genet, 11: 1195-1206). Described herein is the identification of a modifier gene of retinal degeneration.

Retinal degenerative diseases leading to progressive and significant vision loss are the primary cause of blindness throughout the world. Advances in whole genome sequencing technology have led to the identification of mutations responsible for syndromic and nonsyndromic retinal diseases in at least 191 distinct genes. The nuclear hormone receptor NR2E3, also known as photoreceptor-specific nuclear receptor (PNR), has emerged as a significant regulator of photoreceptor cell development and function and is associated with numerous retinal degenerations. Specifically, NR2E3 functions in photoreceptor differentiation by suppressing expression of cone-specific genes and activating rod-specific genes, thereby committing precursors to a rod cell fate (Cheng et al., 2004 Hum Mol Genet, 13: 1563-1575; Haider et al., 2006 Vis Neurosci, 23: 917-929; Peng et al., 2005 Hum Mol Genet, 14: 747-764; Corbo, J. C. & Cepko, C. L., 2005 PLoS Genet, 1: ell; Cheng et al., 2006 Hum Mol Genet, 15: 2588-2602; Webber et al., 2008 Exp Eye Res, 87: 35-48). NR2E3 is also expressed in mature photoreceptors where it regulates expression of genes essential for proper function, such as phototransduction genes (Webber et al., 2008 Exp Eye Res, 87: 35-48; Haider et al., 2009 Exp Eye Res, 89: 365-372). Mutations in human NR2E3 have been associated with several diseases characterized by progressive retinal degeneration, such as enhanced S-cone syndrome (ESCS), Goldmann-Favre syndrome and retinitis pigmentosa (Haider et al., 2000 Nat Genet, 24: 127-131; Schorderet, D. F. & Escher, P., 2009 Hum Mutat, 30: 1475-1485; Gerber et al., 2000 Hum Genet, 107: 276-284; Sharon et al., 2003 Arch Ophthalmol, 121: 1316-1323; Coppieters et al., 2007 Am J Hum Genet, 81: 147-157; Gire et al., 2007 Mol Vis, 13: 1970-1975). Significant phenotypic variation has been observed in patients with NR2E3-associated retinal degeneration, with variable expressivity in patients harboring the same mutation and within the same pedigree, suggesting that genetic modifiers modulate disease outcome in these patients (Schorderet, D. F. & Escher, P., 2009 Hum Mutat, 30: 1475-1485; Escher et al., 2009 Hum Mutat, 30: 342-351; Bandah et al., 2009 Arch Ophthalmol, 127: 297-302).

The retinal degeneration 7 (rd7) mouse is a model for Nr2e3 associated retinal disease (Akhmedov et al., 2000 Proc Natl Acad Sci USA, 97: 5551-5556; Haider et al., 2001 Hum Mol Genet, 10: 1619-1626). The Nr2e3$^{rd7/rd7}$ mouse model was utilized to study the genetic heterogeneity observed in Nr2e3 associated retinal degeneration and to identify genetic modifiers that contribute to such variation. Homozygous rd7 mice develop retinal dysplasia, with whorls and rosettes apparent at postnatal day 10 (P10) and retinal spots detectable by fundus examination at eye opening (P14) (Akhmedov et al., 2000 Proc Natl Acad Sci USA, 97: 5551-5556; Haider et al., 2001 Hum Mol Genet, 10: 1619-1626; Yanagi et al., 2002 Invest Ophthalmol Vis Sci, 43: 3489-3494). Similar to patients with Nr2e3 mutations, rd7 mice exhibit significant increase of S-cones and progressive degeneration of rod and cone photoreceptor cells (Haider et al., 2001 Hum Mol Genet, 10: 1619-1626). The Nr2e3$^{rd7/rd7}$ phenotype is highly variable depending on genetic background (Haider et al., 2008 Mamm Genome, 19: 145-154). Complete penetrance was observed in the B6.Cg-Nr2e3$^{rd7/rd7}$ strain, while suppression occurs in crosses with the genetically divergent and inbred strains AKR/J, CAST/EiJ and NOD.NOH-H2$^{nb1}$; revealing that modifier genes are conferring resistance or susceptibility to the Nr2e3$^{rd7/rd7}$ phenotypes (Haider et al., 2008 Mamm Genome, 19: 145-154).

As described herein, the nuclear hormone receptor Rev-erb alpha, hereafter referred to as Nr1d1, was identified as a genetic modifier of Nr2e3$^{rd7/rd7}$ A locus on chromosome 11 linked to Nr2e3$^{rd7/rd7}$ suppression was genetically fine mapped in the AKR/J background. Through sequence analysis, two strain specific variations in the Nr1d1 gene within this locus were identified. Furthermore, mRNA expression of Nr1d1 is increased in AKR/J retinas compared to C57BL/6J (B6), suggesting that differential levels of NR1D1 modulate rd7 penetrance. As described below, delivery of the Nr1d1 gene to the retinas of B6.Cg-Nr2e3$^{rd7/rd7}$ mice rescues clinical spotting, retinal dysplasia, and molecular changes associated with Nr2e3 loss, confirming that increased Nr1d1 expression is sufficient for suppressing rd7. Most importantly, it was determined that by increasing Nr1d1 expression through gene delivery, key genes within the Nr2e3-directed network are now re-regulated, thereby restoring sufficient normalization of the network to ameliorate disease. Thus, NR1D1 is a potent therapeutic target for Nr2e3-associated retinal degeneration that can compensate for Nr2e3 loss by regulating key molecular pathways associated with disease.

It was determined that Nr1d1 is a genetic modifier gene able to ameliorate Nr2e3 associated retinal degeneration. The Nr2e3$^{rd7/rd7}$ mouse model is completely penetrant in the C57BL/6J genetic background, while suppression of retinal degeneration is observed in the AKR/J background (Akhmedov et al., 2000 Proc Natl Acad Sci USA, 97: 5551-5556; Haider et al., 2008 Mamm Genome, 19: 145-154). The genetic modifier locus linked with rd7 suppression was fine-mapped to a 3.3 cM region containing Nr1d1 and subsequently identified two Nr1d1 sequence variations between C57BL/6J and AKR/J: one in the promoter region and one in the ligand-binding domain of Nr1d1. The present study demonstrates that a single delivery of the Nr1d1 gene to the retina of B6.Cg-Nr2e3$^{rd7/7rd7}$ animals is sufficient to suppress Nr2e3-associated retinal degeneration. Rescue of the rd7 phenotype was observed by fundus and histological examinations of eyes electroporated with Nr1d1 expression vector. As described below, gene delivery experiments with Nr1d1 alleles from both AKR/J and C57BL/6J were able to rescue rd7, suggesting that increased Nr1d1 levels, rather than the nature of the allele, are responsible for the observed suppression.

NR1D1 has been described as a co-factor of NR2E3 and functions in the same transcriptional network as NR2E3 (Cheng et al., 2004 Hum Mol Genet, 13: 1563-1575; Haider et al., 2009 Exp Eye Res, 89: 365-372; Mollema et al., 2011 PLoS One, 6: e17494). A group of genes that are co-targeted by both NR2E3 and NR1D1 was previously identified. Further, previous results show that acute knockdown of NR1D1 by shRNA targeting in the mouse retina results in phenotypes similar to rd7, such as pan-retinal spotting and loss of photoreceptor function (Mollema et al., 2011 PLoS One, 6: e17494). The present study confirms that NR1D1 and NR2E3 act synergistically to regulate genes involved in retinal development and function. These processes are strictly and temporally regulated by key transcription factors directing expression of gene networks both during development and in the mature retina. Misregulation or mutations in genes involved in these processes, such as Nr2e3, disrupt this balance and result in retinal defects. Importantly, delivery of Nr1d1 resulted in molecular changes that restore a balance in the transcriptional networks by normalizing gene expression, thus leading to rescue of retinal integrity and function in rd7 animals. Specifically, it was observed that Nr1d1 delivery results in rescue of expression of the cone phototransduction genes Opn1sw and Gnat2, which are misregulated in rd7. This data indicates that NR1D1 suppresses defects associated with NR2E3 loss through a compensatory mechanism.

The data presented herein illustrate the powerful potential of modifier genes for treatments for inherited retinal disease. As described herein, rescue of retinal integrity and function was achieved through a gene therapy approach by delivering a modifier gene rather than replacing the disease-causing gene. Gene therapy clinical trials have resulted in tremendous success for treating patients with Leber's congenital amaurosis (LCA), an inherited retinal degeneration disease (Maguire et al., 2008 N Engl J Med, 358: 2240-2248; Cideciyan et al., 2009 Hum Gene Ther, 20: 999-1004; Cideciyan et al., 2009 N Engl J Med, 361: 725-727; Simonelli et al., 2010 Mol Ther, 18: 643-650; Jacobson et al., Arch Ophthalmol, 130: 9-24). These studies have led to great advancements towards the use of gene therapy in the clinic; however, prior to the invention described herein, gene replacement studies have not yielded a plethora of therapeutics. The alternate approach described herein identifies genetic modifiers that suppress disease caused by a number of different genes that converge on specific nodes or pathways within a signaling network. As genes function in networks and not singularly, the impact of any gene delivery is on the network as a whole rather than just a single gene. These studies illustrate that viable therapeutic options which have broad impact emanate from genetic modifier genes that are capable of modulating a disease state by impacting entire gene networks that regulate specific biological processes rather than a single gene.

Example 1: Identification of Genetic Modifiers as Therapeutic Targets for Retinal Disease: Rev-Erb Alpha Ameliorates Nr2e3-Associated Retinal Degeneration As described in detail in the Examples below, retinal degenerative diseases are the leading cause of blindness throughout the world. Described herein is the identification of genetic modifiers of retinal degeneration in the rd7 mouse model, which lacks a functional Nr2e3 gene, and the investigation of their potential as therapeutic targets. Described in detail below is the identification of Nr1d1 (also known as Rev-erb alpha) as a genetic modifier of Nr2e3 associated retinal degeneration. The rd7 modifier locus was mapped to a 3.3 cM region in chromosome 11 and it was determined that Nr1d1 was one of three nuclear receptor genes within the modifier locus. Sequence variants between affected and suppressed animals were identified only in Nr1d1. In vivo delivery of Nr1d1 to rd7 retinas rescued retinal degeneration associated with Nr2e3 loss. The rescue was observed not only at the clinical and histological level, but importantly at the functional and molecular level as well such that Nr1d1 was able to restore normal vision to rd7 animals by normalizing key genes within the Nr2e3-directed transcriptional network. Together, these findings uncover Nr1d1 as a therapeutic target for the treatment of retinal degenerative diseases caused by loss of function of Nr2e3. The materials and methods utilized in this example are described in detail below.

Animal Maintenance

Animals were housed in vivariums at the Schepens Eye Research Institute and the Nebraska. Medical Center, use and procedures were approved by the Animal Care and Use Committee and conducted in compliance with the Animal Welfare Act Regulations. C57BL/6J and AKR/J mice were obtained from Jackson Laboratories, Bar Harbor, Me. B6.Cg-Nr2e3$^{rd7/rd7}$ has been previously described (Haider et al., 2008 Mamm Genome, 19: 145-154). B6.Cg-Mor7$^{AKR}$: Nr2e3$^{rd7/rd7}$ mice were generated by outcrossing B6.Cg-Nr2e3$^{rd7/rd7}$×AKR/J F$_2$ mice to C57BL/6J, followed by backcrossing of the F$_2$ progeny to C57BL/6J for six consecutive generations. Genotyping for the Nr2e3$^{rd7/rd7}$ mutation was performed as previously described (Haider et al., 2001 Hum Mol Genet, 10: 1619-1626). Construction of Expression Vectors

```
cDNA from C57BL/6J or AKR/J mice was used to
amplify the Nr1d1^B6 and Nr1d1^AKR/J alleles, as
well as the Nr2e3^B6 allele with the following
primers:
Nr1d1 (F: TTTTTAAGCTTCATCACAACCTCCAGTTTGTGTC (SEQ

ID NO: 1); R: TTTTTAAGCTTGGCGTCCACCCGGAAGGACAGCA (SEQ ID NO: 2))

and

Nr2e3 (F: TTTTTAAGCTTGCAAGCAGGCTACCC TTAGGACC (SEQ

ID NO: 3); R: TTTTTAAGCTTGAACATGTCACACAGGAGCTTCT (SEQ ID NO: 4)). Amplified sequences were cloned into the pAcGFP1-N1 plasmids.
```

In Vivo Electroporation

Nr1d1 allele specific constructs (designated as GFP.Nr1d1$^{B6}$ and GFP.Nr1d1$^{AKR/J}$) were delivered subretinally into the right eye of P0.5 Nr2e3$^{rd7/rd7}$ mice using the electroporation method developed by Matsuda (Matsuda, T. & Cepko, C. L. 2007 Proc Natl Acad Sci USA, 104: 1027-1032). The Nr2e3 allele from C57B6L/J (GFP.Nr2e3$^{B6}$) was electroporated into rd7 animals as a positive control, while electroporation of empty GFP expression vector or no injection to the left eye served as a negative control. 1 μg of naked cDNA was injected subretinally, followed by in vivo electroporation immediately after the injection. Tweezer electrodes were used to hold the head of the pup and five square 80V pulses of 50 ms duration, with 950 ms intervals, were applied using a square wave electroporator. Mice were aged to P30.5 and phenotyped by indirect ophthalmoscopy, electroretinogram (ERG), and immunohistochemistry (Haider et al., 2006 Vis Neurosci, 23: 917-929).

Clinical Examination

Animals were examined by indirect ophthalmology at P30 as previously described (Haider et al., 2008 Mamm Genome, 19: 145-154). Pupils of animals were dilated with 1% Atropine and a Keeler Vantage indirect ophthalmoscope with a 60-diopter lens was used for fundus examinations.

Quantitative Real Time PCR

Gene expression analysis was performed using quantitative RT-PCR as previously described (Haider et al., 2009 Exp Eye Res, 89: 365-372). In brief, retinas were dissected rapidly after eye enucleation and placed in Trizol (Invitrogen) for RNA extraction. Two micrograms of total RNA was reverse transcribed using Retroscript (Ambion). Real-time PCR was performed in technical triplicates with a minimum of three biological replicates using SYBR Green PCR master mix (Applied Biosystems). Reactions were quantified using a Roche 480 LightCycler real time PCR instrument. Relative expression levels were normalized to the amount of β-actin expressed and fold change relative to wild-type C57BL/6J control was calculated using the delta Ct method.

Electroretinography

Electroretinogram analysis was performed on 7 mice of each strain (4 month-old), as described previously (Haider et al., 2008 Mamm Genome, 19: 145-154). Mice were anesthetized with an intraperitoneal injection of a saline carrier (10 mg/g body weight) containing ketamine (1 mg/mL) and xylazine (0.4 mg/mL). Mice were dark adapted for at least six hours and then anesthetized prior to recording. Dark-adapted responses were recorded to short wavelength (λmax=470 nm; Wratten 47A filter) flashes of light over a 4.0 log unit range of intensities (0.3 log unit steps) up to the maximum allowable by the photic stimulator. Light-adapted responses were obtained with white flashes (0.3 step) on the rod-saturating background after 10 min of exposure to the background light to allow complete light adaptation. Signal processing was performed using EM for Windows v7.1.2. Signals were sampled every 0.8 ms over a response window of 200 ms. Responses were computer averaged for each stimulus condition with up to 50 records for the weakest signals.

Preparation of cDNA Loaded Nanoparticles

The nanoparticles were formulated using the previously described double emulsion solvent evaporation method (Aukunuru et al., 2003 J Pharm Pharmacol, 55(9):1199-206; Singh et al., 2009 Gene Ther, 16(5):645-59). The biodegradable polymer used was Poly(L-lactide-co-glycolide)(PLGA) Resomer 503H (50:50; i.v. 0.44 dl/g; Boehringer Ingelheim, Petersburg, Va.). After preparing nanoparticles, drug loading, encapsulation efficiency and particle size were determined.

Administration of cDNA Loaded Nanoparticles cDNA loaded Nile red PLGA nanoparticles are introduced into postnatal day 0 (P0) eyes by intravitreal or subretinal injection, and in some instances the injection was followed by electroporation. Particles were reconstituted in 1×PBS and animals received 1.5 μg of modifier gene cDNA into the right eyes and the same dose of control (empty) nanoparticles into the left eyes at P0. The total volume injected was 0.5 μl. The efficacy of delivery was assessed using Nile red as a nanoparticle tracking dye, and green fluorescent protein expression as a marker of transfected cells. Mice were aged to P30.5 and phenotyped by indirect ophthalmoscopy, electroretinogram (ERG), and immunohistochemistry (Haider et al., 2006 Vis Neurosci, 23: 917-929).

Statistical Analysis

Statistical analysis for FIGS. 2A-2F and 4 was performed using the two-tailed Student's t test, with significance defined as P<0.05. At minimum, 3 biological replicates were included in the each study.

A detailed description of the results of this example is provided below.

Genetic Fine Mapping of Rd7 Modifier Locus on AKR/J Chromosome 11

Previous results revealed that genetic background strongly influences penetrance of Nr2e3$^{rd7/rd7}$ phenotypes (Akhmedov et al., 2000 Proc Natl Acad Sci USA, 97: 5551-5556; Haider et al., 2008 Mamm Genome, 19: 145-154). Specifically, complete suppression of rd7 retinal degeneration was observed in outcrosses of B6. Cg-Nr2e3$^{rd7/rd7}$ mice to AKR/J, CAST/EiJ or NOD.NOH-H2$^{nb1}$ mice ((Haider et al., 2008 Mamm Genome, 19: 145-154). A genome wide scan identified several modifier loci that were unique for each strain (Haider et al., 2008 Mamm Genome, 19: 145-154). To determine if a single modifier gene is able to ameliorate rd7 associated retinal degeneration, an incipient congenic strain that harbors the AKR/J modifier locus on chromosome 11, named Mor7 for modifier of rd7, was generated by backcrossing F2 progeny from the B6.Cg-Nr2e3$^{rd7/rd7}$×AKR/J cross to the C57BL/6J inbred strain for six consecutive generations. Approximately 65% of the B6.Cg-Mor7$^{AKR}$:Nr2e3$^{rd7/rd7}$N6 F$_2$ animals homozygous for the rd7 mutation showed a suppressed phenotype, compared to 49% of F2 animals in the initial intercross of B6.Cg-Nr2e3$^{rd7/rd7}$×AKR/J, suggesting a single modifier gene may be sufficient to suppress rd7. A genome wide analysis of the F$_2$ pups confirmed that approximately 95% of the B6.Cg-Mor7$^{AKR}$:Nr2e3$^{rd7/rd7}$ genome harbored C57BL/6J alleles in the N6 generation (Silver, L. M. *Mouse Genetics: Concept and Applications*, (1995)). Two-thirds of the B6. Cg-Mor7$^{AKR}$:Nr2e3$^{rd7/rd7}$ suppressed mice were heterozygotes across the Mor7 locus, indicating that the AKR/J Mor7 allele acts as a dominant protective allele. Consistent with previous results, the suppressed B6.Cg-Mor7$^{AKR}$:Nr2e3$^{rd7/rd7}$ mice harboring the modifier allele showed restored retinal morphology (FIG. 1A and FIG. 1B) and expression of S-cone opsin (OPN1SW), compared to affected littermates harboring the susceptible allele (FIG. 1C and FIG. 1D). Through fine mapping analysis, the Mor7 suppressor locus was refined to a 3.3 cM region in chromosome 11. This region is flanked by markers D11Mit145 and D11Mit360 and contains approximately 200 genes.

Identification of Nr1d1 as a Genetic Modifier of Rd7

Figure 2A:
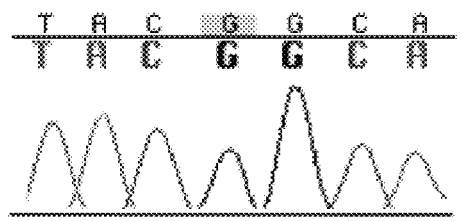
FIGS. 2A-2F are a series of chromatograms and sequence alignments showing strain specific expression of Nr1d1.
Figure 2B:
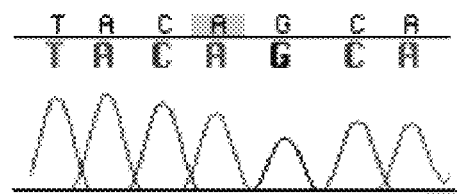

A candidate approach was utilized to identify the Mor7 gene responsible for conferring rd7 suppression. Through rigorous in silico analysis using several resources, it was determined that 95 of the approximately 200 genes that lie within the Mor7 locus are expressed in the retina, 10 of which are transcription factors (FIG. 1E). Three of these genes: thyroid hormone receptor alpha (Thra), retinoid acid receptor alpha (Rara) and rev-erb alpha (Nr1d1) are, like Nr2e3, members of the nuclear hormone receptor family. As described herein, the Mor7 modifier gene functions in the same or parallel pathway as Nr2e3. Further, given that several members of this family have been described as key regulators of retinal development and function, Thra, Rara and Nr1d1 were considered strong candidates for Mor7 and their coding as well as upstream regions were sequenced to identify allelic variants between C57BL/6J and AKR/J. While allelic variants were not found in either Thra or Rara, two single nucleotide polymorphisms (SNPs) were identified in Nr1d1 (FIG. 2). The SNPs identified in Nr1d1 were in both the translated and un-translated regions of the gene. A non-synonymous SNP at position 1222 bp was identified in Nr1d1, resulting in replacement of the consensus Arginine at position 408 by Glutamine in the AKR/J NR1D1 protein (FIG. 2A and FIG. 2B). Sequence alignment of the Nr1d1 gene across species revealed that the consensus for the SNP in the coding region is in accordance with the C57BL/6J sequence (FIG. 2B). This SNP is located within the highly conserved ligand-binding domain of this nuclear hormone receptor. Specifically, the SNP lies within the co-repressor N-CoR binding domain, also known as X domain (Zamir et al., 1996 Mol Cell Biol, 16: 5458-5465).

Figures 2C, 2D:
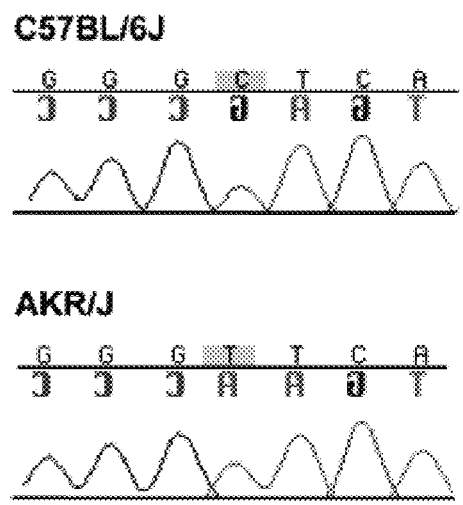
Figure 2E:
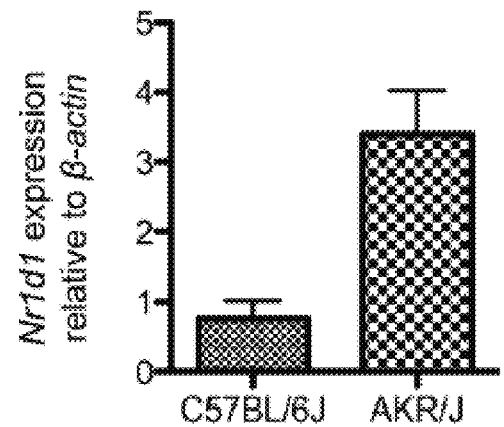
Figure 2F:
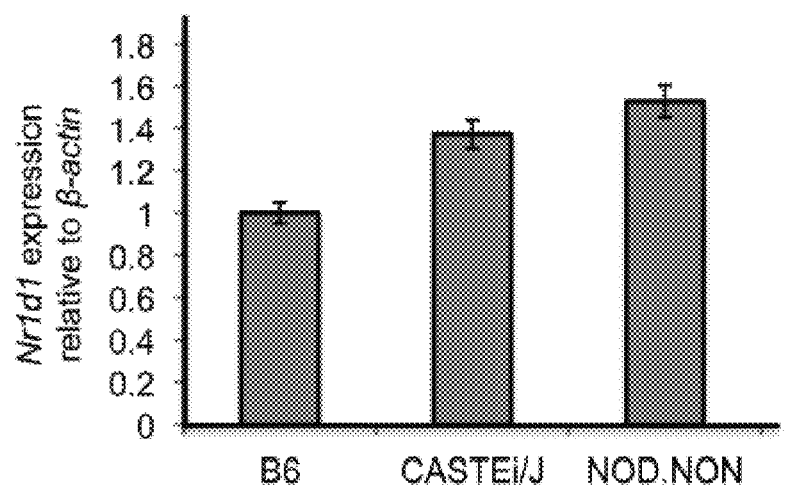

A second SNP was identified at position +494 bp from the putative transcriptional start site (FIG. 2C and FIG. 2D), within the Nr1d1 promoter region (Adelmant et al., 1996 Proc Natl Acad Sci USA, 93: 3553-3558; Kakizawa et al., 2007 J Mol Endocrinol, 38: 555-568). Specifically, the AKR/J genome harbors a thymidine whereas a cytosine residue is found in C57BL/6J. Sequence alignment of the Nr1d1 gene across species revealed that the consensus nucleotide for this location corresponds to thymidine, which is in accordance with the AKR/J sequence (FIG. 2D). As this SNP resides within the promoter region of Nr1d1, it was examined whether Nr1d1 mRNA expression varies in B6 versus AKR/J retinas. Quantitative real time PCR confirmed that Nr1d1 mRNA expression is up-regulated by 3 fold in the AKR/J retina, compared to C57BL/6J ($P=0.0024$, FIG. 2E). This difference in expression may account for the suppressed effect observed in AKR/J genetic background.

Nr1d1 Delivery Restores Retinal Integrity in Rd7

NR1D1 regulates many processes such as differentiation, metabolism, and the circadian rhythm (Burris, T. P. 2008 Mol Endocrinol, 22: 1509-1520). More recently, results have demonstrated a role for NR1D1 in the retina. NR1D1 forms a complex with NR2E3, CRX and NRL, key transcriptional regulators of retinal development and function (Walia et al., 2008 Arch Ophthalmol, 126: 379-384). In addition, recent results have identified a number of targets co-regulated by NR2E3 and NR1D1 in the developing and adult retina (Cheng et al., 2004 Hum Mol Genet, 13: 1563-1575; Mollema et al., 2011 PLoS One, 6: e17494). Thus, Nr1d1 is a strong candidate to modify the effects of Nr2e3 associated retinal degeneration.

Figure 3A:
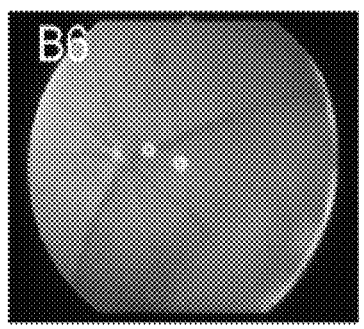
Figure 3B:
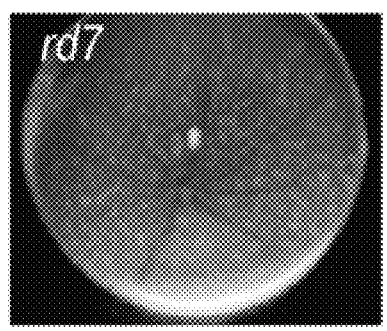
Figure 3C:
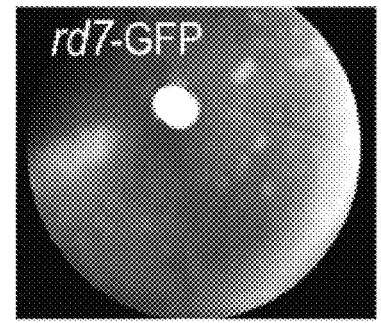
Figure 3D:
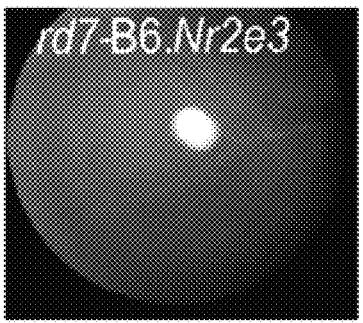
Figure 3E:
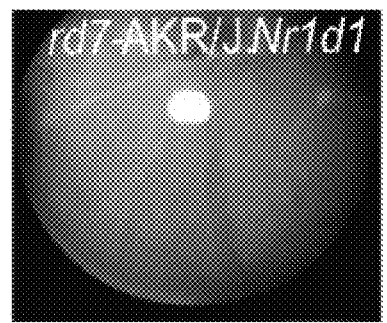
Figure 3F:
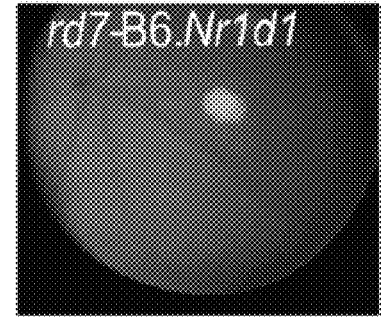
Figure 3G:
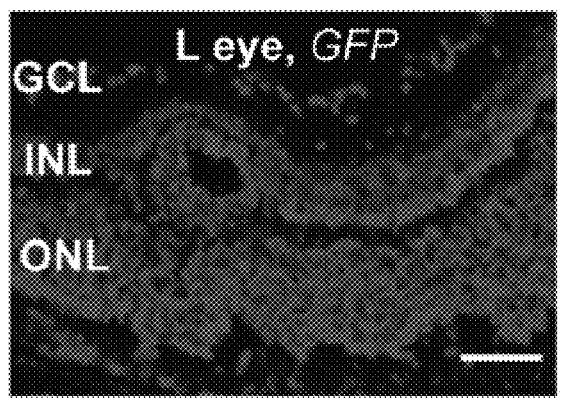
Figure 3H:
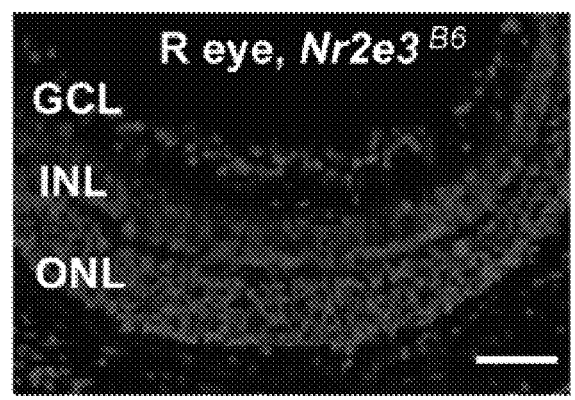
Figure 3I:
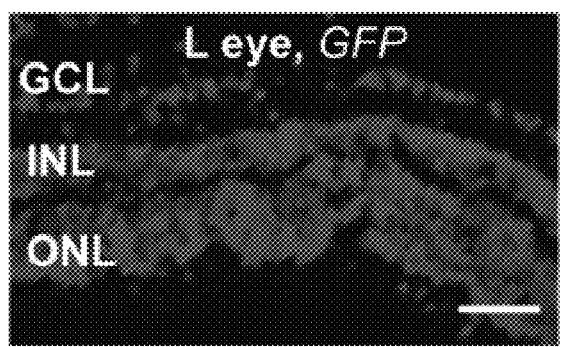
Figure 3J:
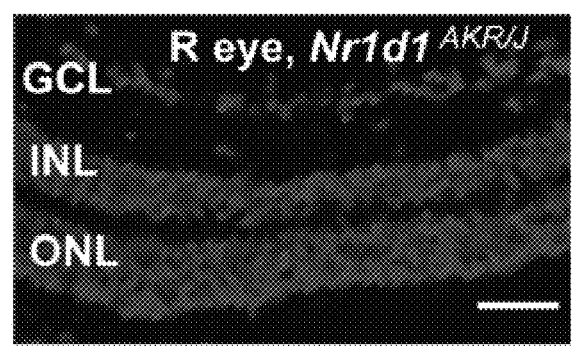
Figure 4:
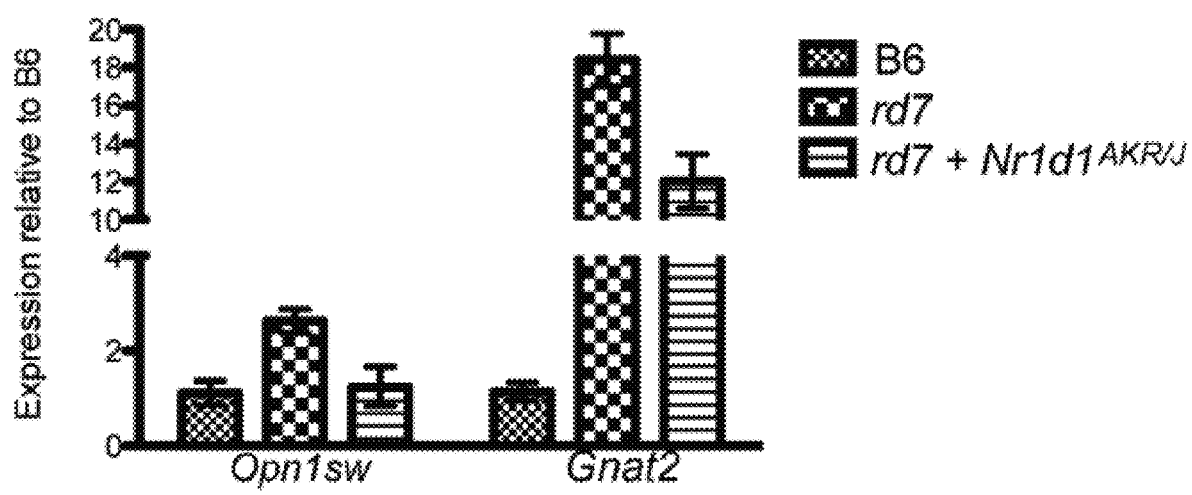
FIG. 4 is a bar chart showing that expression of phototransduction genes Opn1sw and Gnat2 is rescued in rd7 retinas upon Nr1d1 delivery. Quantitative real time PCR shows that Nr1d1 delivery results in down-regulation of Opn1sw and Gnat2 in rd7 retinas normalizing gene expression (n=3, p<0.05).

In vivo electroporation was performed to deliver Nr1d1 alleles from either C57BL/6J or AKR/J into the retina of neonatal rd7 mice to determine whether NR1D1 can modulate rd7 associated retinal degeneration. One month after injection, animals were examined clinically by indirect ophthalmoscopy for detection of the characteristic rd7 pan-retinal spotting. While spotting of the fundus was clearly observable in the eyes electroporated with the control GFP vector at P30.5, electroporation of GFP.Nr2e3$^{B6}$ resulted in suppression of the phenotype (FIG. 3C and FIG. 3D). Delivery of either GFP.Nr1d1$^{B6}$ or GFP.Nr1d1$^{AKR/J}$ also resulted in rescue of the pan-retinal spotting phenotype (FIG. 3E and FIG. 3F). Further, the absence of retinal spotting correlated with absence of retinal dysplasia in histological sections (FIGS. 3G-3J). A subset of the electroporated animals were aged to 4 months and electroretinograms (ERGs) were performed to examine visual function. Significant improvements in both scotopic (dark-adapted) and photopic (light-adapted) ERG response were observed in B6.Cg-Nr2e3$^{rd7/rd7}$ eyes injected with GFP.Nr1d1$^{AKR/J}$, compared to GFP injected eyes (FIG. 3K and FIG. 3L). These studies demonstrate that the dosage of Nr1d1 is sufficient for rescue of Nr2e3-associated retinal disease irrespective of allelic variants in the ligand-binding domain; thus the promoter SNP is likely the protective allele, mediating rescue of disease.

Mechanism of Nr1d1-Mediated Suppression Through Molecular Rescue of Rd7 Mis-Regulated Genes NR1D1, a regulator of circadian clock metabolism, also functions as a cofactor of NR2E3 and regulates expression of a number of genes in the retina (Cheng et al., 2004 Hum Mol Genet, 13: 1563-1575; Mollema et al. 2011 PLoS One 6, e17494). The expression profile of the retinas of rd7 animals was previously characterized, and 30 genes that are misregulated in Nr2e3 deficient retinas were identified, 24 of which are directly regulated by NR2E3, NR1D1 or co-regulated by both receptors (Haider et al., 2009 Exp Eye Res, 89: 365-372). As described in detail below, it was determined that NR1D1 is able to suppress rd7 associated retinal degeneration through molecular rescue of key developmental and functional pathways that are misregulated in the rd7 retina.

As the level of misregulation varied greatly for all 30 genes, the expression of Opn1sw (the S-cone specific opsin) and Gnat2 (cone photoreceptor specific transducin) (key components of the cone phototransducion cascade that are significantly up-regulated in rd7) was evaluated. Quantitative RT-PCR was performed to assay expression of Opn1sw and Gnat2 in the retina of rd7 animals 30 days after GFP.Nr1d1$^{AKR/J}$ delivery. Expression of Opn1sw was 1.5 fold increased in the retina of untreated rd7 animals (left eye, n=3) compared to C57BL/6J, consistent with previous reports ($p=0.004$, FIG. 4). GFP.Nr1d1$^{AKR/J}$ delivery to the right eye of the same rd7 animals resulted in a significant reduction in Opn1sw expression ($p=0.035$, FIG. 4). Furthermore, Opn1sw levels in GFP.Nr1d1$^{AKR/J}$ injected eyes were not significantly different from those present in C57BL/6J retinas ($p=0.86$), indicating that Nr1d1 delivery rescues Opn1sw expression to near normal levels. Gnat2 was also significantly decreased in eyes injected with GFP.Nr1d1$^{AKR/J}$, compared to uninjected eyes from the same animals ($p=0.005$, FIG. 4). These results indicate that Nr1d1 up-regulation is able to suppress Nr2e3 associated retinal degeneration by compensating for Nr2e3 loss in the retina and by redirecting the biological networks that modulate photoreceptor development and function.

Example 2: Nr1d1 Rescues Retinal Degeneration 1 (Rd1), a Mouse Model for Severe Autosomal Dominant Retinitis Pigmentosa Retinitis pigmentosa (RP) is an inherited, degenerative eye disease that causes severe vision impairment and often blindness in an estimated 1 in 1,000 individuals in the U.S. population. Mutations in the human pde6b gene cause autosomal dominant RP, an Nr2e3-associated retinal disease. The retinal degeneration 1 (rd1) mouse is a model for a severe form of RP and comprises a mutation in the mouse pde6b gene.

Figure 5:
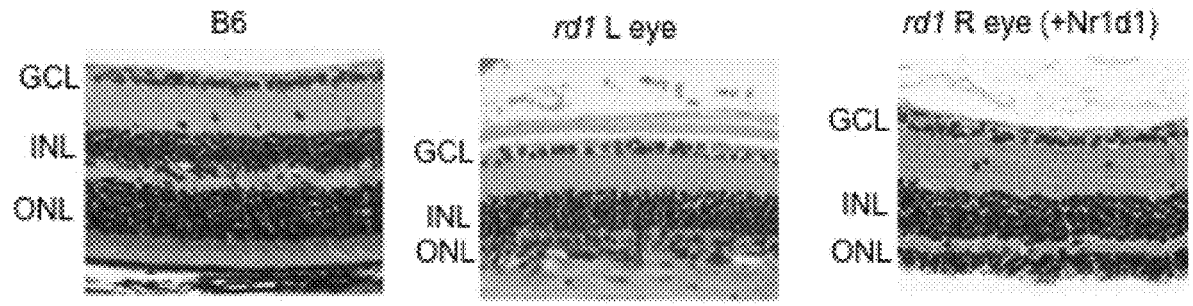
FIG. 5 is a series of photomicrographs showing rescue of retinal degeneration 1 (rd1), a mouse model for severe autosomal dominant retinitis pigmentosa. B6=control/wild type eye. rd1 L eye=left eye of rd1 mouse. rd1 R eye (+Nr1d1)=right eye of rd1 mouse rescued with Nr1d1.
Figure 6A:
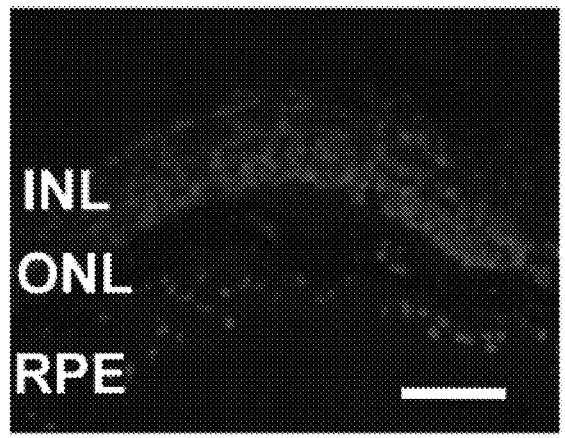
FIG. 6A and FIG. 6B are a series of photomicrographs showing the GFP expression in P30 rd7 retina electroporated with GFP.Nr1d1$^{AKR/J}$.
Figure 6B:
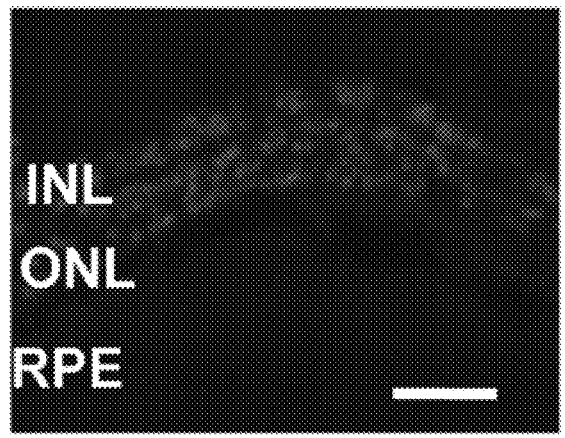

As show in in FIG. 5, Nr1d1 rescues phenotype in the rd1 mouse. Specifically, as compared to the B6 control eye, the retina of the left eye (no gene therapy) of the rd1 mouse does not have any photoreceptor cells in the outer nuclear layer (ONL). By contrast, the retina of the right eye of the rd1 mouse after rescue with Nr1d1 comprises about 40-50% more photoreceptor cells in the ONL, as compared to the left eye (no gene therapy).

The sequence alignment below shows an Nr1d1 variant observed in a human patient with an Nr2e3 mutation. The patient had a milder phenotype (i.e., retinal degeneration) to begin with. The Nr1d1 variant illustrated below is located in the promoter region of Nr1d1, similar to the mouse variant that confers resistance to Nr2e3 associated retinal degeneration.

```
                         -346 bp
                            |
Human         GAGCTCCAGATTCGCCACCCCGCAGCGCTG    SEQ ID NO: 13

Chimpanzee    GAGCTCCAGATTCGCTACCCCGCAGCGCTG    SEQ ID NO: 14
```

```
                        -continued
Dog         GAGCTCCAGATTCGCTACCCTGCAGCGCTG    SEQ ID NO: 13

Cow         GAGCTCCAGATTCGATACCCTGCAGCGCTG    SEQ ID NO: 16

Mouse       GAGCTCCAGATTCATTACCCTGCTTCACTG    SEQ ID NO: 17
            *************  ****  **  *  ***
```

Example 3: Nanoparticle Delivery and Rescue in Rd7 Mouse Model

Preparation of cDNA Loaded Nanoparticles

The nanoparticles were formulated using the previously described double emulsion solvent evaporation method (Aukunuru J V 2003, Singh SR 2009). The biodegradable polymer used was Poly(L-lactide-co-glycolide)(PLGA) Resomer 503H (50:50; i.v. 0.44 dl/g; Boehringer Ingelheim, Petersburg, Va.). After preparing nanoparticles, drug loading, encapsulation efficiency and particle size were determined.

Administration of cDNA Loaded Nanoparticles cDNA loaded Nile red PLGA nanoparticles are introduced into postnatal day 0 (P0) eyes by intravitreal or subretinal injection, and in some instances the injection was followed by electroporation. In brief, particles were reconstituted in 1×PBS and animals received 1.5 ug of modifier cDNA into the right eyes and the same dose of control (empty) nanoparticles into the left eyes at P0. The total volume injected was 0.5 ul. The efficacy of delivery was assessed using Nile red as a nanoparticle tracking dye, and green fluorescent protein expression as a marker of transfected cells. Mice were aged to P30.5 and phenotyped by indirect ophthalmoscopy, electroretinogram (ERG), and immunohistochemistry (Haider et al 2006). Half of the animals injected with nanoparticles were then subjected to electroporation of the eye to test for enhancement of nanoparticles uptake based on the degree of the rd7 phenotype recovery.

Results

Figure 7A:
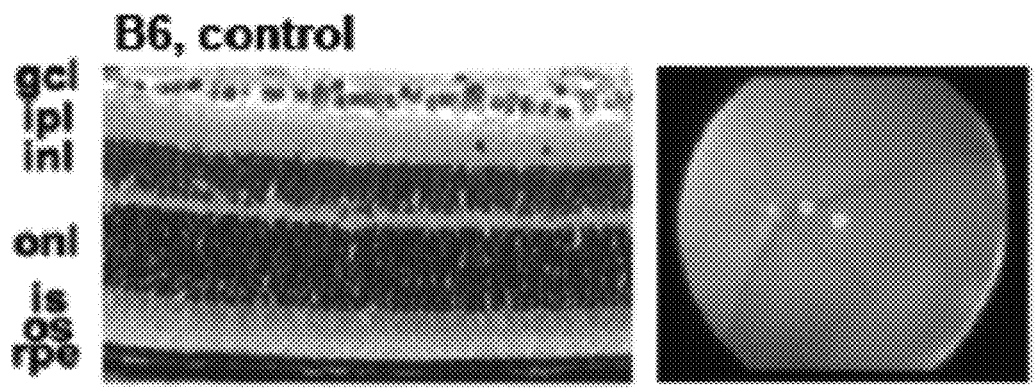
FIG. 7A and FIG. 7B are a series of pictomicrographs showing histology (left panels) and fundus photography (right panels) of eyes from rd7 mice.
Figure 7B:
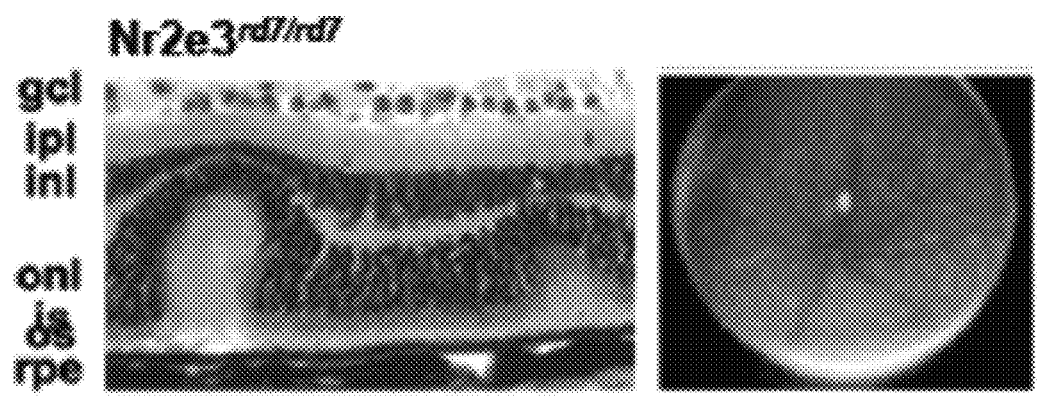

The phenotype of the rd7 mouse model includes: appearance of white spots in the retina (FIG. 7B, right panel), retinal whorls and rosettes in the outer nuclear layer (FIG. 7B, left panel), electroretinograms show reduction in cone and rod signals after 5 months, cone and rod cell loss causes reduction of ONL thickness by half, and significant increase in the percentage of cone cells expressing blue opsin.

Figure 8:
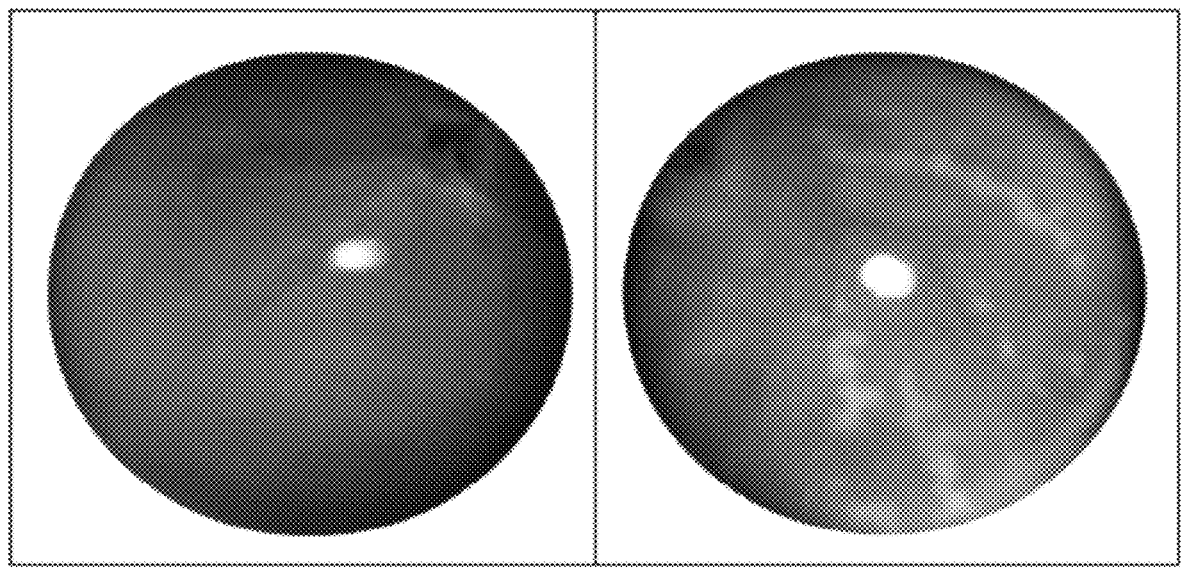
FIG. 8 is two fundus photography images showing the retinas of rd7/rd7 mice injected with either blank vector (right panel) or Nr2e3 vector (left panel).
Figure 9A:
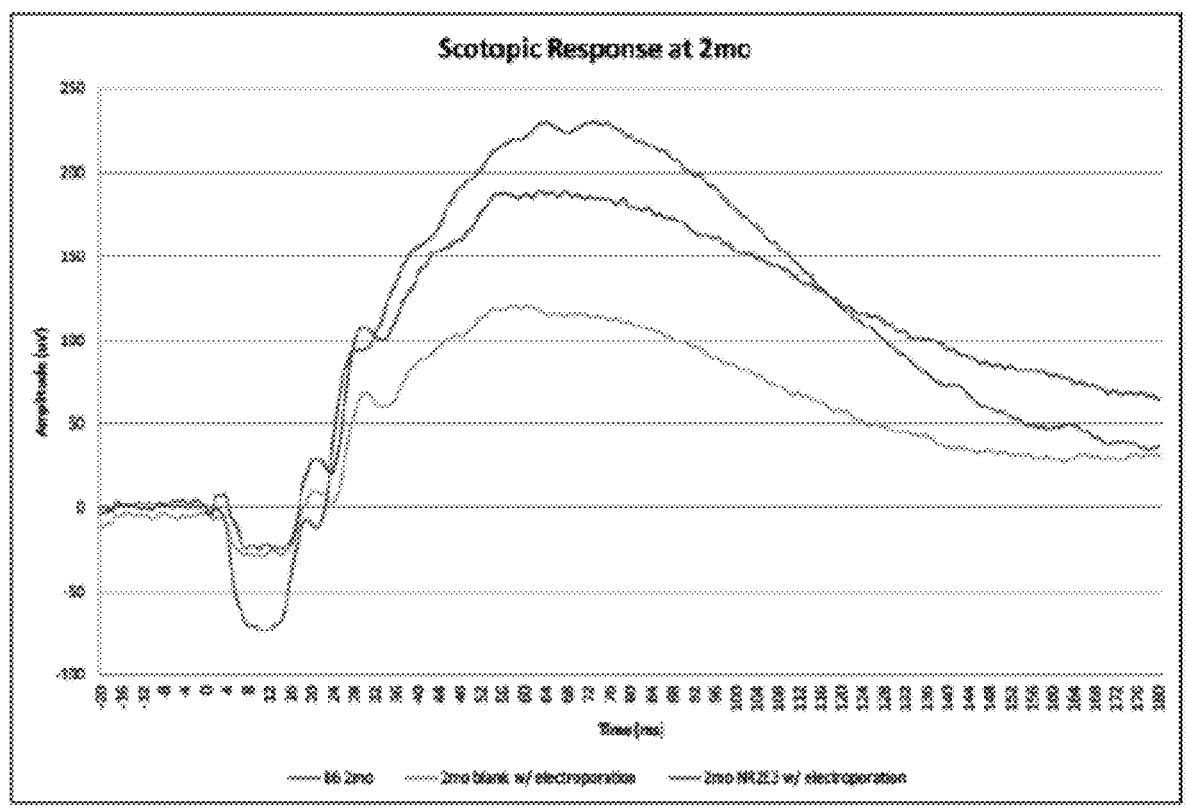
FIG. 9A and FIG. 9B are two electroretinograms depicting the results of scotopic analysis of rd7 mice comparing mice that received blank vector or Nr2e3 vector at FIG. 9A) 2 months or FIG. 9B) 6 months.
Figure 9B:
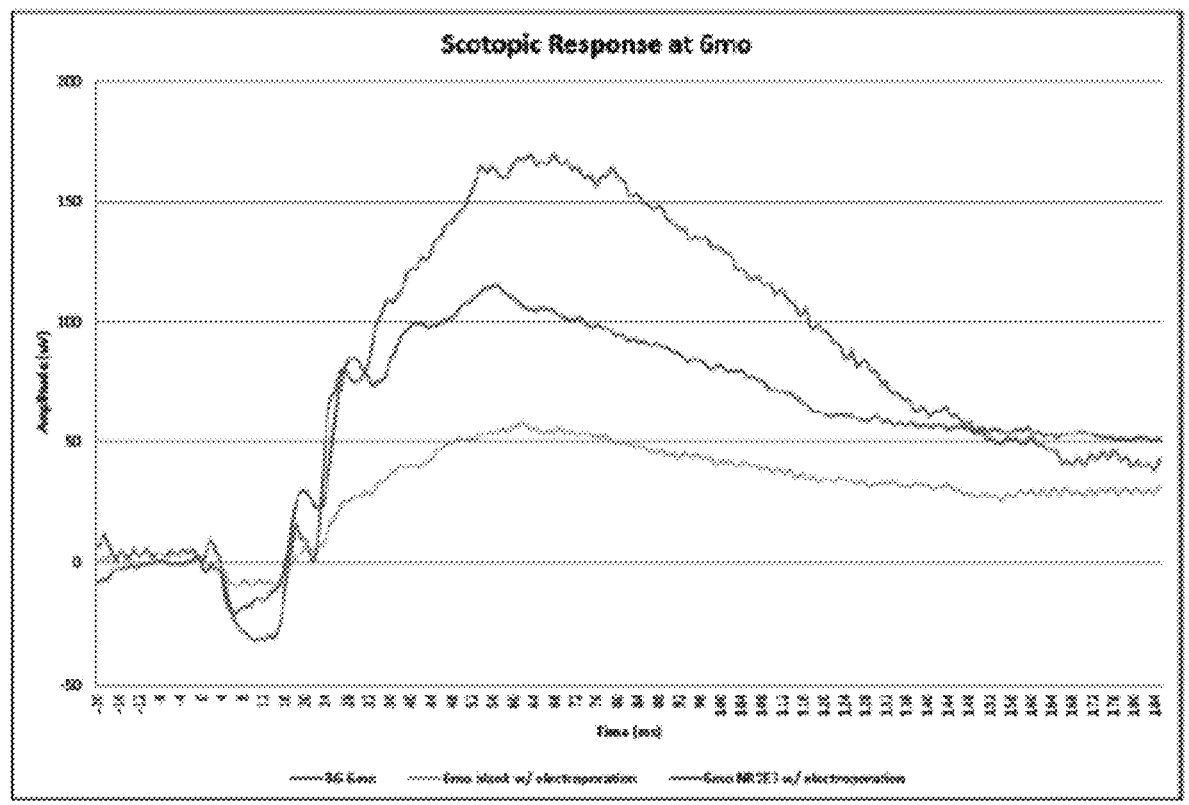
Figure 10:
FIG. 10 is a schematic showing the domains of nuclear hormone receptors, such as Nr2e3.

Mutant rd7 retinas treated with Nr2e3 nanoparticles exhibited clinical improvements with the disappearance of the characteristic rd7 spotted retina and morphologically with rescue of rd7 associated whorls and rosettes. Specifically, fundus examinations were performed to determine gross phenotypic differences between treated and untreated retinas. While spotting of the fundus was clearly observable when rd7 mice were injected with blank vector, administration of Nr2e3-containing nanoparticles reduced the severity of spotting and provided a partial recovery of the phenotype (FIG. 8).

Electroretinograms were performed under both photopic and scotopic conditions to further assess nanoparticle effectiveness. These assessments were performed in animals of 2 months of age and 6 months of age. ERG analysis showed a significantly improved amplification of both a and b wave of the treated eyes compared to the reduced function observed in untreated rd7 eyes.

These results demonstrate that rescue of rd7 associated retinal degeneration was attained in both electroporated and nonelectroporated Nr2e3 nanoparticle treated mutant eyes. Nanoparticle delivery of Nr2e3 in the rd7 mice efficiently ameliorated clinical, morphological, and functional defects associated with rd7 retinal degeneration. Further, evaluation of the efficacy of delivery with and without electroporation demonstrated that particles are able to enter and function in the retina effectively without electroporation.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating an ocular disease or disorder associated with a retinal degenerative disease in a subject in need of such a treatment, said method consisting of administering to said subject a composition consisting of a pharmaceutically-acceptable carrier and a therapeutically effective amount of a nucleic acid encoding a nuclear hormone receptor ("NHR") to an ocular or adnexal tissue of the subject to increase the expression of said NHR thereby treating said ocular disease or disorder in said subject, wherein said NHR is selected from the group consisting of NR2E3, RORA, NUPR1, NR2C1, and a combination thereof, and wherein said composition is administered locally to said ocular or adnexal tissue.

2. The method of claim 1, wherein said nuclear hormone receptor is NR2E3.

3. The method of claim 1, wherein said ocular disease or disorder comprises retinitis pigmentosa, age related macular degeneration, and inherited retinal degenerative diseases.

4. The method of claim 1, wherein said ocular disease or disorder comprises retinal degeneration.

5. The method of claim 1, wherein said NHR consists of a full-length nucleic acid encoding NHR.

6. The method of claim 1, wherein said NHR comprises NR2E3.

7. The method of claim 6, wherein said nucleic acid encoding NR2E3 comprises SEQ ID NO: 7.

8. The method of claim 1, wherein said NHR comprises RORA.

9. The method of claim 6, wherein said nucleic acid encoding RORA comprises SEQ ID NO: 9.

10. The method of claim 1, wherein said NHR comprises NUPR1.

11. The method of claim 6, wherein said nucleic acid encoding NUPR1 comprises SEQ ID NO: 28.

12. The method of claim 1, wherein said NHR comprises NR2C1.

13. The method of claim 6, wherein said nucleic acid encoding NR2C1 comprises SEQ ID NO: 12.

14. The method of claim 1, wherein said composition is administered via electroporation, biodegradable poly(lactide-co-glycolide) (PLGA) nanoparticle-based gene delivery, nanosystem based delivery systems (liposomes, dendrimers, nanocomplexes), naked DNA delivery, small molecule-based gene delivery, viral-based gene delivery, or a combination thereof.

15. The method of claim 1, wherein said viral-based gene delivery is adeno-associated virus gene delivery.

16. The method of claim 1, wherein said nucleic acid is administered intravitreally, subretinally, topically, intravenously or a combination thereof.

17. The method of claim 1, further comprising, prior to administering the treatment, identifying a subject suffering from or at risk of developing retinal degeneration or retinal dysplasia, or a combination thereof.

18. The method of claim 1, wherein the composition consists of a pharmaceutically-acceptable carrier and a therapeutically effective amount of a nucleic acid encoding.

\* \* \* \* \*